US012600821B2

(12) United States Patent
Abe et al.

(10) Patent No.: US 12,600,821 B2
(45) Date of Patent: Apr. 14, 2026

(54) CROSSLINKED ORGANOSILICON RESIN, A METHOD FOR PRODUCING SAME, AND A COSMETIC

(71) Applicant: Shin-Etsu Chemical Co., Ltd., Tokyo (JP)

(72) Inventors: Takuya Abe, Annaka (JP); Masayuki Konishi, Tokyo (JP); Chihiro Hayakawa, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 328 days.

(21) Appl. No.: 18/417,229

(22) Filed: Jan. 19, 2024

(65) Prior Publication Data

US 2024/0166823 A1 May 23, 2024

Related U.S. Application Data

(62) Division of application No. 17/258,786, filed as application No. PCT/JP2019/027183 on Jul. 9, 2019, now Pat. No. 11,912,828.

(30) Foreign Application Priority Data

Jul. 11, 2018 (JP) ................................ 2018-131538

(51) Int. Cl.

| | |
|---|---|
| ***C08G 77/38*** | (2006.01) |
| ***A61K 8/895*** | (2006.01) |
| ***A61Q 1/00*** | (2006.01) |
| ***A61Q 1/06*** | (2006.01) |
| ***A61Q 1/10*** | (2006.01) |
| ***A61Q 3/02*** | (2006.01) |
| ***A61Q 5/06*** | (2006.01) |
| ***A61Q 5/12*** | (2006.01) |
| ***A61Q 15/00*** | (2006.01) |
| ***A61Q 17/04*** | (2006.01) |

(52) U.S. Cl.

CPC .............. *C08G 77/38* (2013.01); *A61K 8/895* (2013.01); *A61Q 1/00* (2013.01); *A61Q 1/06* (2013.01); *A61Q 1/10* (2013.01); *A61Q 3/02* (2013.01); *A61Q 5/06* (2013.01); *A61Q 5/12* (2013.01); *A61Q 15/00* (2013.01); *A61Q 17/04* (2013.01); *A61K 2800/31* (2013.01)

(58) Field of Classification Search

None

See application file for complete search history.

(56) References Cited

U.S. PATENT DOCUMENTS

| | | | |
|---|---|---|---|
| 2008/0311060 | A1 | 12/2008 | Sakuta et al. |
| 2010/0247460 | A1 | 9/2010 | Lin et al. |
| 2011/0077344 | A1 | 3/2011 | Hasegawa et al. |
| 2013/0150535 | A1 | 6/2013 | Griswold |
| 2013/0295028 | A1 | 11/2013 | Lee et al. |
| 2015/0073059 | A1 | 3/2015 | Knoer et al. |
| 2016/0251482 | A1 | 9/2016 | Yamazaki et al. |
| 2018/0118988 | A1 | 5/2018 | Kuroda |
| 2018/0215877 | A1 | 8/2018 | Hori et al. |
| 2018/0298148 | A1 | 10/2018 | Abe et al. |

FOREIGN PATENT DOCUMENTS

| | | | |
|---|---|---|---|
| JP | H07196449 | A | 8/1995 |
| JP | H09143029 | A | 6/1997 |
| JP | H09175940 | A | 7/1997 |
| JP | 2000086429 | A | 3/2000 |
| JP | 2008115358 | A | 5/2008 |
| JP | 2009052038 | A | 3/2009 |
| JP | 2010540721 | A | 12/2010 |
| JP | 2015505878 | A | 2/2015 |
| JP | 2015515981 | A | 6/2015 |
| JP | 2015519426 | A | 7/2015 |
| JP | 2016155967 | A | 9/2016 |
| JP | 2016204598 | A | 12/2016 |
| JP | 2017075283 | A | 4/2017 |
| WO | 2017018358 | A1 | 2/2017 |

OTHER PUBLICATIONS

English translation of International Search Report corresponding to International Patent Application No. PCT/JP2019/027183 (3 pages) (mailed Oct. 8, 2019).

*Primary Examiner* — Nicole P Babson

(74) *Attorney, Agent, or Firm* — Myers Bigel, P.A.

(57) ABSTRACT

Described herein is a crosslinked organosilicone resin that has a crosslinked structure formed by reacting a silicone or hydrocarbon having an alkenyl group at both ends thereof with a hydrosilyl group-containing organosilicone resin, is soluble with a liquid oil at room temperature, and forms a film by volatilization of the oil. Also described herein is a method for preparing a crosslinked organosilicone resin and cosmetics containing a crosslinked organosilicone resin.

11 Claims, No Drawings

CROSSLINKED ORGANOSILICON RESIN, A METHOD FOR PRODUCING SAME, AND A COSMETIC

TECHNICAL FIELD

The present invention relates to a crosslinked organosilicone resin and a cosmetic containing the same.

BACKGROUND OF THE INVENTION

Organosilicone resins essentially have three-dimensional structures composed of a Q unit ($SiO_{4/2}$) and T unit ($RSiO_{3/2}$) (R is, for example, a monovalent organic group). They are characteristic of favorable weather resistance, heat resistance, water repellency, and electrical insulation, so that they have conventionally been used as an intermediate raw material for pressure sensitive adhesives, rubber compounds, mold release agents, and coating agents. In recent years, some organosilicone resins have an increasing demand as a raw material for cosmetics such as foundations, lip sticks, eyeshadows, creams, milky lotions, and hair cosmetics because of their film-forming property. They are also usable as a viscosity enhancing agent for improving shape stability of emulsified products or lip sticks. For example, in Patent Literatures 1 and 2, an organosilicone resin dissolved in a cyclic silicone is compounded in a cosmetic to provide an effect of suppressing makeup deterioration caused by sweat or sebum secreted from the skin or color transfer caused by secondary adhesion.

As described above, organosilicone resins compounded in cosmetic improve makeup retention. There are however two problems in compounding an organosilicone resin in a cosmetic. First, a film formed is brittle. A film formed by applying a cosmetic containing an organosilicone resin to hair, face, or hands cannot follow slight movement of a substrate and may cause cracks or dropping-off. In particular, a MQ resin composed of M units ($R_3SiO_{1/2}$) and Q units ($SiO_{4/2}$) is very rigid and, therefore, has good mechanical strength, but has difficulty in forming a self-standing film due to its brittleness. In contrast to the MQ resin, a MTQ, MDQ, MDTQ, or DT resin having a T unit or D unit introduced therein has improved film flexibility and forms a strong self-standing film which follows movement of a substrate. However, it still maintains the rigidity of the resin and has a problem in abrasion resistance. Patent Literature 3 describes that a crack-free film may be formed by applying an emulsion containing a plasticized MQ resin to the hair. However, when a silicone gum is incorporated as a plasticizer, the resulting emulsion has deteriorated film strength and, further, has increased adhesion to cause unpleasantness such as stickiness, and thus impairs the feeling in use.

The second problem is less oil resistance. A cosmetic to be applied to the skin is required to have resistance to the sebum. The sebum is composed mainly of a hydrocarbon oil, an ester oil, and triglyceride. An organosilicone resin used as a film-forming component causes such a problem that the organosilicone resin has high compatibility with such oils so that the film swells over time after application of the cosmetic and its physical strength deteriorates, leading to deterioration in makeup retention. On the other hand, since a silicone-modified acrylic polymer has higher oil resistance than an organosilicone resin, a composition using both an organosilicone resin and a silicone-modified acrylic polymer has been proposed (Patent Literature 4: Japanese Patent Application Laid-Open No. Hei 7-196449). Although the silicone-modified acrylic polymer forms a soft film and the composition may provide a film somewhat flexible and able to follow movement of a substrate, the film does not have satisfactory oil resistance and is therefore not effective for improving the makeup retention.

In recent years, a crosslinked organosilicone resin obtained by crosslinking an organosilicone resin with a silicone has been reported. This is used in a variety of applications such as pressure sensitive adhesives, self-adhesives, coating agents, and personal care products. Patent Literature 5 describes that a crosslinked organosilicone resin is prepared by heat-curing a vinyl-containing organosilicone resin and a hydrosilyl-containing silicone to provide a cured product having a high flexibility. The resin has however no solubility in a volatile oil and is therefore not suited for use as a film-forming component. Patent Literatures 6 and 7 describe similar crosslinked organosilicone resins, but they are of gel and lack a film-forming ability. According to Patent Literature 8, a crosslinked organosilicone resin is prepared by reacting a hydrosilyl group-containing organosilicone resin with a vinyl-containing silicone. The cured product obtained is however tacky and has low solubility in a volatile oil.

PRIOR ART LITERATURES

Patent Literatures

Patent Literature 1: Japanese Patent Application Laid-Open No. Hei 9-143029

Patent Literature 2: Japanese Patent Application Laid-Open No. Hei 9-175940

Patent Literature 3: Japanese National Phase Publication No. Hei 27-515981

Patent Literature 4: Japanese Patent Application Laid-Open No. Hei 7-196449

Patent Literature 5: Japanese Patent Application Laid-Open No. Hei 21-052038

Patent Literature 6: Japanese National Phase Publication No. 2010-540721

Patent Literature 7: Japanese National Phase Publication No. 2015-519426

Patent Literature 8: Japanese National Phase Publication No. 2015-505878

SUMMARY OF THE INVENTION

Problems to be Solved by the Invention

The present invention has been made in the above-described circumstances. An object of the invention is to provide a crosslinked organosilicone resin which has a crosslinked structure formed by reacting a silicone or hydrocarbon having an alkenyl group at both ends with a hydrosilyl group-containing organosilicone resin, is soluble with a liquid oil at room temperature, and forms a film by volatilization of the oil, and to provide a method for preparing the crosslinked organosilicone resin and cosmetics containing the crosslinked organosilicone resin.

Means for Solving the Problems

The present inventors have made intensive researches in order to achieve the aforesaid object and have found that a crosslinked organosilicone resin which is solid at 25 degrees C. and soluble in an oil liquid at room temperature is obtained by specifying an amount of a hydrosilyl group of a hydrosilyl group-containing organosilicone resin which is a raw material of a crosslinked organosilicone resin and specifying a chain length of a silicone or hydrocarbon having an alkenyl group at both ends as a crosslinking agent. A dissolved form of such a crosslinked organosilicone resin is also provided. It has also been found that when the oil is a volatile oil, the crosslinked organosilicone resin dissolved in an oil is formed a film by volatilizing the oil and, thus, it may be used as a film-forming component; and that whereas the organosilicone resin before crosslinked forms a rigid film with brittleness, the crosslinked organosilicone resin has lower brittleness to provide a flexible film without tackiness, leading to the completion of the present invention.

The present invention provides a crosslinked organosilicone resin represented by the following average composition formula (1):

$$(R^1{}_3SiO_{1/2})_{a1}(R^2{}_3SiO_{1/2})_{a2}(R^3{}_3Si_{1/2})_{a3}(R^1{}_{3-p}(X_{1/2})_pSiO_{1/2})_{a4}(R^1{}_2SiO_{2/2})_b(R^1SiO_{3/2})_c(SiO_{4/2})_d \quad (1)$$

wherein $R^1$ is, independently of each other, a substituted or unsubstituted, monovalent hydrocarbon group having 1 to 30 carbon atoms and having no aliphatic unsaturated bond, $R^2$ is, independently of each other, a polyoxyalkylene-containing group, a polyglycerin-containing group, or a group selected from the groups defined for $R^1$ and at least one of $R^2$ in each of the $R^2{}_3SiO_{1/2}$ units is a polyoxyalkylene-containing group or a polyglycerin-containing group, $R^3$ is, independently of each other, an organopolysiloxane-containing group or a group selected from the groups defined for $R^1$ and at least one of $R^3$ in each of the $R^3{}_3SiO_{1/2}$ units is an organopolysiloxane-containing group, X is a divalent group represented by the following formula (2) or (3):

(2)

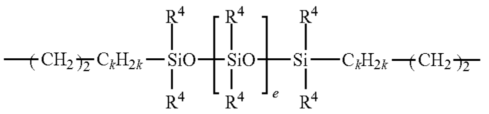

wherein $R^4$ is, independently of each other, a substituted or unsubstituted, monovalent hydrocarbon group having 1 to 30 carbon atoms and having no aliphatic unsaturated bond, e is an integer of $0 \le e \le 500$ and k is an integer of $0 \le k \le 5$;

$$(CH_2)_2—C_fH_{2f}—(CH_2)_2— \quad (3)$$

wherein f is an integer of $0 \le f \le 20$;

optionally, a part of $R^2$, $R^3$ and X may be a hydroxyl group, a1, a2, a3, a4, b, c, and d satisfy the equations, $0 \le a1 \le 400$, $0 \le a2 \le 200$, $0 \le a3 \le 400$, $0 \le a4 \le 50$, $0 \le b \le 320$, $0 \le c \le 320$, $0 \le d \le 1{,}000$ and $0.5 \le (a1+a2+a3+a4)/d \le 1.5$ and p is an integer of $1 \le p \le 3$.

Effects of the Invention

The crosslinked organosilicone resin of the present invention has ability of forming a strong and flexible film. Cosmetics comprising the organosilicone resin compounded provide a good feeling in use, have long makeup retention, are superior in spread and finish appearance, and have excellent rub-off resistance.

In particular, it has generally been believed that a hard film has low flexibility and a highly flexible film tends to be soft and, thus, is a contradictory relationship between strength and flexibility in films. A film of the crosslinked organosilicone resin of the present invention however has high flexibility and excellent ability to follow movement of a substrate, while it is a strong film. Further, compared to a resin before modified, the organosilicone resin of the present invention has highly improved resistance to an oil such as sebum. Non-crosslinked organosilicone resins tend to have improved oil resistance with an increased molecular weight. However, this improvement is limitative, because it is limitative to increase a molecular weight of non-crosslinked organosilicone resin. Thus, the improvement of the oil resistance is limitative. The crosslinking of an organosilicone resin with a crosslinking agent increases a molecular weight of the organosilicone resin in a sense to enhance the improvement of oil resistance. The crosslinked organosilicone resin of the present invention therefore has good oil resistance that cannot be achieved by conventional non-crosslinked organosilicone resins. In addition, a cosmetic containing the present resin as a film-forming component does not give tackiness when applied, and provides a comfortable feeling in use, shows long makeup retention (duration) because of its excellent water resistance and oil resistance and good adhesion to the skin, good spreadability and finish appearance, and excellent rub-off resistance to prevent secondary adhesion.

DETAILED DESCRIPTION OF THE INVENTION

The present invention will hereinafter be described in detail.

A crosslinked organosilicone resin represented by the following average composition formula (1):

$$(R^1{}_3SiO_{1/2})_{a1}(R^2{}_3SiO_{1/2})_{a2}(R^3{}_3Si_{1/2})_{a3}(R^1{}_{3-p}(X_{1/2})_pSiO_{1/2})_{a4}(R^1{}_2SiO_{2/2})_b(R^1SiO_{3/2})_c(SiO_{4/2})_d \quad (1)$$

wherein $R^1$ is, independently of each other, a substituted or unsubstituted, monovalent hydrocarbon group having 1 to 30 carbon atoms and having no aliphatic unsaturated bond, $R^2$ is, independently of each other, a polyoxyalkylene-containing group, a polyglycerin-containing group, or a group selected from the groups defined for $R^1$ and at least one of $R^2$ in each of the $R^2{}_3SiO_{1/2}$ units is a polyoxyalkylene-containing group or a polyglycerin-containing group, $R^3$ is, independently of each other, an organopolysiloxane-containing group or a group selected from the groups defined for $R^1$ and at least one of $R^3$ in each of the $R^3{}_3SiO_{1/2}$ units is an organopolysiloxane-containing group, X is a divalent group represented by the following formula (2) or (3):

(2)

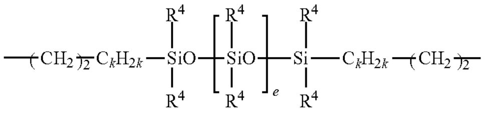

wherein $R^4$ is, independently of each other, a substituted or unsubstituted, monovalent hydrocarbon group having 1 to 30 carbon atoms and having no aliphatic unsaturated bond, e is an integer of $0 \le e \le 500$ and k is an integer of $0 \le k \le 5$;

$$(CH_2)_2—C_fH_{2f}—(CH_2)_2— \quad (3)$$

wherein f is an integer of $0 \le f \le 20$;

optionally, a part of $R^2$, $R^3$ and X may be a hydroxyl group, a1, a2, a3, a4, b, c, and d satisfy the equations, $0 \le a1 \le 400$, $0 \le a2 \le 200$, $0 \le a3 \le 400$, $0 \le a4 \le 50$, $0 \le b \le 320$, $0 \le c \le 320$, $0 \le d \le 1{,}000$ and $0.5 \le (a1+a2+a3+a4)/d \le 1.5$ and p is an integer of $1 \le p \le 3$.

In the formula, $R^1$ is, independently of each other, a substituted or unsubstituted, monovalent hydrocarbon group having 1 to 30 carbon atoms, preferably 1 to 10 carbon atoms, and having no aliphatic unsaturated bond. Examples of $R^1$ include alkyl groups having 1 to 30 carbon atoms, aryl groups and aralkyl groups and groups in which the hydrogen atom bonded to the carbon atom of aforesaid groups are substituted with a halogen atom, an amino group, or a carboxyl group. Among these, preferred are alkyl groups having 1 to 10 carbon atoms, aryl groups and aralkyl groups, fluorine-substituted alkyl groups, chloro-substituted alkyl groups, amino-substituted alkyl groups, and carboxyl-substituted alkyl groups. Specifically, examples include methyl group, ethyl group, propyl group, butyl group, pentyl group, cyclopentyl group, cyclohexyl group, phenyl group, tolyl group, trifluoropropyl group, heptadecafluorodecyl group, chloropropyl group, and chlorophenyl group. Particularly preferred are an alkyl group having 1 to 5 carbon atoms, a phenyl group and a trifluoropropyl group.

$R^2$ is, independently of each other, a polyoxyalkylene-containing group, a polyglycerin-containing group, or a group selected from the groups for $R^1$ and, at least one of $R^2$ in each of the $R^2{}_3SiO_{1/2}$ units is a polyoxyalkylene-containing group or a polyglycerin-containing group. $R^3$ is as described above. A part of $R^2$ and $R^3$ may be a hydroxyl group.

The polyoxyalkylene-containing group is preferably represented by the following formula (4):

$$—(CH_2)_2—C_mH_{2m}—O—(C_2H_4O)_{g1}(C_3H_6O)_{g2}R^5 \quad (4)$$

wherein $R^5$ is an unsubstituted or substituted, monovalent hydrocarbon group having 1 to 30 carbon atoms or a hydrogen atom; and m, g1 and g2 are integers of $0 \le m \le 15$, $0 \le g1 < 200$, $0 \le g2 < 200$, and $0 < g1+g2 \le 200$.

The polyglycerin-containing group is preferably represented by the following formula (5):

$$—(CH_2)_2—C_mH_{2m}—O—(CH_2CH(OH)CH_2O)_hR^5 \quad (5)$$

wherein $R^5$ is an unsubstituted or substituted, monovalent hydrocarbon group having 1 to 30 carbon atoms or a hydrogen atom; and m and h are integers of $0 \le m \le 15$ and $0 < h \le 5$.

$R^5$ is, independently of each other, an unsubstituted or substituted, monovalent hydrocarbon group having 1 to 30 carbon atoms or a hydrogen atom. Preferred are alkyl groups having 1 to 10 carbon atoms, more preferably 1 to 5 carbon atoms and a hydrogen atom. Examples of the alkyl group include methyl group, ethyl group, propyl group, butyl group, and pentyl group. Additional examples include groups obtained by substituting the hydrogen atom bonded to the carbon atom of aforesaid groups with a halogen atom, amino group, or carboxyl group, such as fluorine-substituted alkyl groups, chloro-substituted alkyl groups, amino-substituted alkyl groups, and carboxyl-substituted alkyl groups.

In the formulas (4) and (5), m is an integer of $0 \le m \le 15$, preferably $0 \le m \le 2$; and g1 is an integer of $0 \le g1 < 200$, preferably $0 \le g1 \le 100$, more preferably $0 \le g1 \le 50$. If g1 is larger than 200, the resulting resin has a lower melting temperature and therefore lacks a film forming property. In the formulas, g2 is an integer of $0 \le g2 < 200$, preferably $0 \le g2 \le 100$, more preferably $0 \le g2 \le 50$. If g2 is larger than 200, the resulting resin has a lower melting temperature and therefore lacks a film forming property. In the formulas, g1+g2 satisfies the equation $0 \le g1+g2 < 200$, preferably $0 \le g1+g2 \le 100$, more preferably $0 \le g1+g2 \le 50$. If g1 and g2 is larger than 50, the resulting resin has a lower melting temperature and therefore lacks a film forming property. When the polyoxyalkylene moiety comprises both ethylene oxide unit and propylene oxide unit, the polyoxyalkylene moiety may be either a block copolymer or random copolymer of the both units. In the formulas, h satisfies the equation, $0 < h \le 5$, preferably $0 < h \le 4$, more preferably $0 < h \le 3$. If h is larger than 5, the resulting resin has a lower melting temperature and therefore lacks a film forming property.

The organopolysiloxane-containing group for $R^3$ is a group represented by the following formula (6), (7), (8), or (9). In each of the $R^3SiO_{1/2}$ units, at least one of $R^3$ is a group represented by the following formula (6), (7), (8) or (9).

$$—(CH_2)_2—C_nH_{2n}—(SiOR^6{}_2)_i—SiR^6{}_3 \quad (6)$$

$$—(CH_2)_2—C_nH_{2n}—SiR^6{}_{j1}—(OSiR^6{}_3)_{3-j1} \quad (7$$

$$—(CH_2)_2—C_nH_{2n}—SiR^6{}_{j1}—(OSiR^6{}_{j2}(OSiR^6{}_3)_{3-j2})_{3-j1} \quad (8)$$

$$—(CH_2)_2—C_nH_{2n}—SiR^6{}_{j1}—(OSiR^6{}_{j2}(OSiR^6{}_{j3}(OSiR^6{}_3)_{3-j3})_{3-j2})_{3-j1} \quad (9)$$

wherein $R^6$ is, independently of each other, a substituted or unsubstituted, monovalent hydrocarbon group having 1 to 30 carbon atoms and having no aliphatic unsaturated bond; n and i are integers satisfying equations, $0 \le n \le 5$ and $0 \le i \le 500$; and $j_1$ to $j_3$ are integers of 0 to 2.

$R^6$ is, independently of each other, a substituted or unsubstituted, monovalent hydrocarbon group having 1 to 30 carbon atoms, preferably 1 to 10 carbon atoms. Examples of $R^6$ include alkyl groups, aryl groups, and aralkyl groups, and these groups wherein a part of the hydrogen atoms bonded to carbon atoms is replaced with a halogen atom, an amino group, or a carboxyl group. More specifically, preferred are alkyl groups, aryl groups, aralkyl groups, fluorine-substituted alkyl groups, chloro-substituted alkyl groups, amino-substituted alkyl groups, and carboxyl-substituted alkyl groups. Specific examples include methyl group, ethyl group, propyl group, butyl group, pentyl group, cyclopentyl group, cyclohexyl group, phenyl group, tolyl group, trifluoropropyl group, heptadecafluorodecyl group, chloropropyl group, and chlorophenyl group. Among these, alkyl groups having 1 to 5 carbon atoms, a phenyl group and a trifluoropropyl group are more preferred.

In the formulas, n satisfies the equation, $0 \le n \le 5$, preferably $0 \le n \le 2$; i satisfies the equation, $0 \le i \le 500$, preferably $1 \le i \le 100$, more preferably $1 \le i \le 50$. If i is larger than 500, the resulting resin has a lower melting temperature and lacks a film forming property. In the formulas, $j_1$ to $j_3$ are integers satisfying the equation, $0 \le j_{1-3} \le 2$.

X is a divalent group represented by the following formula (2) or (3):

(2)

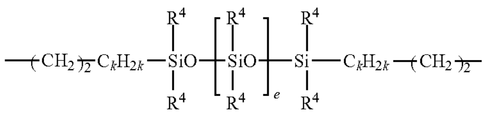

wherein $R^4$ is, independently of each other, a substituted or unsubstituted, monovalent hydrocarbon group having 1 to 30 carbon atoms and having no aliphatic unsaturated bond, e is an integer of $0 \le e \le 500$ and k is an integer of $0 \le k \le 5$;

$$(CH_2)_2—C_fH_{2f}—(CH_2)_2— \qquad (3)$$

wherein f is an integer of $0 \le f \le 20$;

wherein a part of X may optionally be a hydroxyl group and, then, X is monovalent.

In the formula (2), $R^4$ is, independently of each other, a substituted or unsubstituted, monovalent hydrocarbon group having 1 to 30, preferably 1 to 10 carbon atoms, and having no aliphatic unsaturated bond. Examples of $R^4$ include alkyl groups, aryl groups, and aralkyl groups and these groups wherein a part of the hydrogen atoms bonded to carbon atoms is replaced with a halogen atom, an amino group, or a carboxyl group. More specifically, preferred are alkyl groups, aryl groups, aralkyl groups, fluorine-substituted alkyl groups, chloro-substituted alkyl groups, amino-substituted alkyl groups, and carboxyl-substituted alkyl groups. More specific examples include methyl group, ethyl group, propyl group, butyl group, pentyl group, cyclopentyl group, cyclohexyl group, phenyl group, tolyl group, trifluoropropyl group, heptadecafluorodecyl group, chloropropyl group, and chlorophenyl group. Among these, alkyl groups having 1 to 5 carbon atoms, phenyl group and trifluoropropyl group are more preferred.

In the formula (2), e satisfies $0 \le e \le 500$, preferably $0 \le e \le 100$, more preferably $0 \le e \le 50$. If e is larger than the upper limit, a resin has a lower melting temperature and lacks a film forming property. In the formulas, k satisfies the equation, $0 \le k \le 5$, preferably $0 \le k \le 3$, more preferably $0 \le k \le 1$.

In the formula (3), f satisfies the equation, $0 \le f \le 20$, preferably $2 \le f \le 18$, more preferably $4 \le f \le 16$. If f is larger than the upper limit, a resin is brittle.

The crosslinked organosilicone resin of the present invention necessarily has at least one of the group represented by the formula (2) and the group represented by the formula (3). The group represented by the formula (2) has a flexible skeleton so as to provide the organosilicone resin containing with flexibility. The group represented by the formula (3) has a rigid skeleton so as to provide the organosilicone resin with rigidity. Accordingly, physical properties of a film are controllable by regulating a proportion of the group represented by the formula (2) and the group represented by the formula (3). In order to obtain a flexible and self-standing film, the organosilicone resin is preferably composed of at least one of the groups of the formula (2).

The organosilicone resin may comprise two or more kinds selected from the groups represented by the formula (2) or (3). The group of the formula (2) having a longer chain gives more flexibility to the organosilicone resin. The group of the formula (3) having a longer chain gives more rigidity to the organosilicone resin. Therefore, physical properties of a film may be controlled by incorporating two groups of the formula (2) or (3) having different chain lengths.

In the crosslinked organosilicone resin represented by the formula (1), a1, a2, a3, a4, b, c and d are the numbers satisfying the following equations: $0 < a1 \le 400$, preferably $01 < a1 \le 100$, more preferably $1 < a1 \le 50$; $0 \le a2 \le 200$, preferably $0 \le a2 \le 100$, more preferably $0 \le a2 \le 50$; $0 \le a3 \le 400$, preferably $0 \le a3 \le 100$, more preferably $0 \le a3 \le 50$. If a3 is larger than 200, the resulting resin has a lower melting temperature and lacks a film forming property. In the formula, a4 is the number satisfying the following equation: $0 < a4 \le 50$, preferably $0 < a4 \le 30$, more preferably $0 \le a4 \le 10$. If a4 is larger than 50, the resulting resin is likely to cause gelation because of a larger molecular weight due to an increased crosslinking degree. In the formula, b, c, and d are the numbers satisfying $0 \le b \le 320$, $0 \le c \le 320$ and $0 < d \le 1{,}000$, and $0.5 \le (a1+a2+a3+a4)/d \le 1.5$, preferably $0.7 \le (a1+a2+a3+a4)/d \le 1.2$. If the value of $(a1+a2+a3+a4)/d$ is less than the lower limit, the resulting resin is of gel because of a larger molecular weight due to an increased crosslinking degree. If the value exceeds the upper limit, the resulting resin has a smaller molecular weight and lacks a film forming property. In the formula, p is an integer satisfying $1 \le p \le 3$, preferably 1 or 2, particularly preferably 1.

The crosslinked organosilicone resin of the present invention preferably has a weight average molecular weight of from 1,000 to 1,000,000, more preferably from 1,000 to 500,000, more preferably from 3,000 to 300,000. The molecular weight within the aforesaid range is preferred from the standpoint of performance and easy working such as filtration. The weight average molecular weight in the present invention may be determined as a polystyrene-reduced weight average molecular weight in gel permeation chromatography (GPC).

The crosslinked organosilicone resin represented by the average composition formula (1) in which at least one of X is a group represented by the formula (2), a4 satisfies the equation, $0 < a4 \le 5$, and e in the formula (2) is an integer satisfying the equation, $0 < e < 40$, is solid at 25 degrees C. and is excellent in film forming property. If a4 is larger than 5 and e is larger than 40, the resulting resin is likely to be in a gel state after a diluting solvent is removed and, then, the resin has a film forming property, but gives a film of a gel-derived touch.

In particular, when at least one of X is a group represented by the formula (2), a4 satisfies the equation, $0 < a4 \le 3$, and e in the formula (2) is an integer satisfying $0 < e \le 20$, a crosslinked organosilicone resin represented by the average composition formula (1) is solid at 25 degrees C. and superior in film forming property. The film has excellent bending resistance and oil resistance.

[Preparation Method]

A crosslinked organosilicone resin may be synthesized according to various manners known in the art. For example, crosslinking may be caused by reacting an organopolysiloxane having a hydroxyl group at both ends with a surface silanol group of an organosilicone resin. This method has, however, a drawback that due to difficulty in completely controlling the amount of the surface silanol group of the organosilicone resin, it is difficult to precisely control the amount of cross-links with the organopolysiloxane. A crosslinked organosilicone resin may also be synthesized by an addition reaction between an organosilicone resin having an unsaturated group and an organopolysiloxane having a hydrosilyl group at both ends. However, when it is desired to introduce another functional group, types of introducible functional groups are restricted. Therefore, this method is not preferred. Accordingly, synthesis by the addition reaction between an organosilicone resin having a hydrosilyl group and an organopolysiloxane having an unsaturated group at both ends is preferred.

Specifically, the crosslinked organosilicone resin represented by the average composition formula (1) is obtained by hydrosilylating a hydrosilyl group-containing organosilicone resin represented by the following average composition formula (13) and being solid or liquid at 25 degrees C. with at least one of terminal alkenyl group-containing compounds represented by the following formula (11), (12), (14), (15), (16), (17), (18) or (19), with the proviso that the compound (11) is essential.

The hydrosilylation may be conducted in the presence of a platinum catalyst or a rhodium catalyst.

$$(R^1{}_3SiO_{1/2})_{a1}(H_pR^1{}_{3-p}SO_{1/2})_{a2+a3+a4}(R^1{}_2SiO_{2/2})_b(R^1SiO_{3/2})_c(SiO_{4/2})_d \quad (13)$$

wherein $R^1$ is, independently of each other, a substituted or unsubstituted, monovalent hydrocarbon group having 1 to 30 carbon atoms and having no aliphatic unsaturated bond; a1, a2, a3, a4, b, c, and d satisfy the equations, $0<a1\leq 400$, $0<a2\leq 200$, $0\leq a3\leq 400$, $0<a4\leq 50$, $0\leq b\leq 320$, $0\leq c\leq 320$, $0<d\leq 1{,}000$, and $0.5\leq(a1+a2+a3+a4)/d\leq 1.5$, and p is an integer of $1\leq p\leq 3$.

(11)

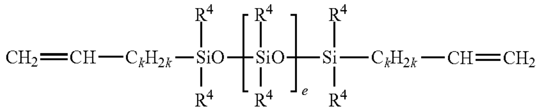

wherein $R^4$, e, and k are as defined above.

$$CH_2{=}CH{-}C_fH_{2f}{-}CH{=}CH_2 \quad (12)$$

wherein f is as defined above.

$$CH_2{=}CH{-}C_mH_{2m}{-}O{-}(C_2H_4O)_{g1}(C_3H_6O)_{g2}R^5 \quad (14)$$

wherein $R^5$, m, g1, and g2 are as defined above.

$$CH_2{=}CH{-}C_mH_{2m}{-}O{-}(CH_2CH(OH)CH_2O)_hR^5 \quad (15)$$

wherein $R^5$, m, and h are as defined above.

$$CH_2{=}CH{-}C_nH_{2n}{-}(SiOR^6{}_2){-}SiR^6{}_3 \quad (16)$$

$$CH_2{=}CH{-}C_nH_{2n}{-}SiR^6{}_{j1}{-}(OSiR^6{}_3)_{3-j1} \quad (17)$$

$$CH_2{=}CH{-}C_nH_{2n}{-}SiR^6{}_{j1}{-}(OSiR^6{}_{j2}(OSiR^6{}_3)_{3-j2})_{3-j1} \quad (18)$$

$$CH_2{=}CH{-}C_nH_{2n}{-}SiR^6{}_{j1}{-}(OSiR^6{}_{j2}(OSiR^6{}_{j3}(OSiR^6{}_3)_{3-j3})_{3-j2})_{3-j1} \quad (19)$$

wherein $R^6$, n, i, and $j_{1-3}$ are as defined above.

The hydrosilyl group-containing organosilicone resin represented by the average composition formula (13) comprises Q unit ($SiO_{4/2}$), M unit ($R^1{}_3SiO_{1/2}$) and ($H_nR^1{}_{3-n}SiO_{1/2}$) as essential units, and may optionally comprise D unit ($R^1{}_2SiO_{2/2}$) and T unit ($R^1SiO_{3/2}$). The resin may be either solid or liquid at 25 degrees C., but is preferably solid from the standpoint of a film-forming property. Examples of the resin include MQ resins, MTQ resins, MDQ resins and MDTQ resins. The weight average molecular weight of the resin is preferably in a range of from 2,000 to 30,000, more preferably in a range of from 3,000 to 15,000, from the standpoint of performance and easy working such as filtration. The weight average molecular weight may be determined as a polystyrene-reduced weight average molecular weight in gel permeation chromatography (GPC).

The method for preparing the crosslinked organosilicone resin by hydrosilylation will be described in further detail below.

In a hydrosilylation between the hydrosilyl group-containing organosilicone resin represented by the average composition formula (13) with the terminal unsaturated group-containing compound represented by the formula (11), (12), (14), (15), (16), (17), (18), or (19), a molar ratio of the hydrosilyl group to the terminal unsaturated group is preferably from 0.5 to 2.0, more preferably from 0.8 to 1.2.

The hydrosilylation is conducted preferably in the presence of a platinum catalyst or a rhodium catalyst. For example, platinic chloride, alcohol-modified platinic chloride, and platinic chloride-vinyl siloxane complex are preferred. If an amount of the catalyst is too much, the resulting product is colored. The catalyst amount is preferably 50 ppm or less, particularly preferably 20 ppm or less, as an amount of platinum or rhodium.

The aforesaid addition reaction may be conducted in the presence of an organic solvent, if needed. Examples of the organic solvent include cyclic organopolysiloxanes such as octamethylcyclotetrasiloxane, decamethylcyclopentasiloxane, and dodecamethylcyclohexasiloxane; aromatic hydrocarbons such as toluene and xylene; ketone-based organic solvents such as acetone, methyl ethyl ketone, diethyl ketone, methyl isobutyl ketone; aliphatic hydrocarbons such as hexane, heptane, octane, and cyclohexane, and aliphatic alcohols such as methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol, and 1,2-propylene glycol. Ethanol, 1-propanol, and 2-propanol are particularly preferred from the standpoint of reactivity.

An amount of the solvent is preferably from 1 to 80% by mass, more preferably from 5 to 50% by mass, based on the whole reaction mixture. Then, the reaction mixture is maintained uniform so that the reaction proceeds efficiently.

Reaction conditions are not particularly limited. Preferably, the reaction mixture is heated under reflux at a temperature of from 50 to 150 degrees C., more preferably from 80 to 120 degrees C., for about 1 to 10 hours.

The addition reaction may be followed by a step of removing the rhodium catalyst or platinum catalyst, using activated carbon. An amount of the activated carbon is preferably from 0.001 to 5.0% by mass, particularly preferably from 0.01 to 1.0% by mass, based on the whole reaction mixture. Then, color of the product is removed.

The addition reaction may be followed by a step of diminishing any remaining hydrosilyl group, if needed. Specifically, when the resin is used in a cosmetic, the step of diminishing a hydrosilyl group is preferably carried out, because the hydrosilyl group may cause dehydrogenation, which is roblematic in view of safety.

In order to diminish the unreacted hydrosilyl group, a basic catalyst such as alkali metal carbonate, alkali metal bicarbonate, or alkali metal hydroxide are added to hydrolyze the unreacted hydrosilyl group and, then, an acidic catalyst of an amount equivalent to the basic catalyst is added to neutralize the latter. Specific examples of the basic catalyst include strongly basic catalysts such as lithium hydroxide, sodium hydroxide, potassium hydroxide, calcium hydroxide, and barium hydroxide; and weakly basic catalysts such as sodium carbonate, calcium carbonate, and sodium bicarbonate. The strongly basic catalyst such as sodium hydroxide is particularly preferred in view of promoting the dehydrogenation. Specific examples of the acid catalyst include hydrochloric acid, sulfuric acid, sulfurous acid, fuming sulfuric acid, oxalic acid, p-toluenesulfonic acid, methanesulfonic acid, trifluoroacetic acid, trifluoromethanesulfonic acid, phosphoric acid, formic acid, acetic acid, propionic acid, benzoic acid, and citric acid. In general, it is preferred to use the base or acid in combination with water, and the reaction system is heated at a temperature not higher than the boiling temperature of water, rather than to use the acid alone or base alone. In this step, the hydrosilyl group (SiH group) is converted into a hydroxysilyl group (SiOH group).

The addition reaction may be followed by a deodorizing treatment for reducing any odor, if needed. Particularly when the resin is to be used in cosmetics, the deodorizing treatment is preferred, because the resin may generate odor over time. Mechanism for a polyether-modified silicone to generate odor is generally explained as follows. When an addition reaction is conducted between allyl-etherified polyether and a hydrogen polyorganosiloxane in the presence of a platinum catalyst, a propenyl-etherified polyether is produced due to internal transition of the allyl group as a side reaction. The propenyl-etherified polyether has no reactivity with the hydrogen polyorganosiloxane and, accordingly, remains as an impurity in the reaction system. When water acts on the propenyl-etherified polyether, the propenyl ether is hydrolyzed to generate propionaldehyde, which has bad odor. It is known that the aforesaid hydrolysis is accelerated by acid. When a polyether-modified silicone is used in a water-based cosmetic, the cosmetic tends to become acidic over time due to the oxidative degradation of the polyether and the hydrolysis is accelerated to generate bad odor.

There are two typical methods for deodorization. The first one is to add an acid catalyst to a solution after the addition reaction to hydrolyze the whole propenyl ether remaining in the reaction system and remove the generated propionaldehyde by strip purification (Japanese Patent No. 2137062).

Examples of the acid catalyst used for the aforesaid first method include hydrochloric acid, sulfuric acid, sulfurous acid, fuming sulfuric acid, oxalic acid, p-toluene sulfonic acid, methane sulfonic acid, trifluoroacetic acid, trifluoromethanesulfonic acid, phosphoric acid, formic acid, acetic acid, propionic acid, benzoic acid, and citric acid. These acids may be used in a combination with water. When removal of the used acid is required, use is preferably made of an acid having a low boiling temperature such as hydrochloric acid, formic acid, acetic acid, or trifluoroacetic acid. From the standpoint of treatment efficiency, a strong acid such as hydrochloric acid or trifluoroacetic acid is preferred.

A treatment temperature is preferably 80 degrees C. or lower to prevent the hydrophilic group from being oxidized. An amount of the acidic aqueous solution is preferably from 0.1 to 100%, more preferably from 5 to 30%, of the organic group-modified organosilicone resin.

From the standpoint of productivity, the aqueous solution is added to adjust the pH of the addition reaction mixture to 7 or less, stirred under heat, and then stripped off. The stripping may be conducted at normal temperature or at a reduced pressure, preferably at 120 degrees C. or lower. For efficient strip at this temperature, the strip is preferably conducted at a reduced pressure. However, when the stripping is conducted at normal pressure, it is preferred to do aeration with an inert gas such as nitrogen or argon.

The second method for deodorization is to subject the addition reaction mixture to hydrogenation to convert the unsaturated double bond to an alkyl group so as to stably suppress the generation of propionaldehyde over time (U.S. Pat. No. 5,225,509, Japanese Patent Application Laid-Open No. Hei 7-330907).

The hydrogenation may be conducted with hydrogen or with a metal hydride, in a homogeneous system or a heterogeneous system. These may be combined. A heterogeneous catalytic hydrogenation with a solid catalyst is most preferred in view of an advantage that the catalyst does not remain in a product.

Examples of the solid catalyst include elements or compounds of nickel, palladium, platinum, rhodium, cobalt, chromium, copper and iron. In these cases, a catalyst carrier is not always necessary. However, if required, a carrier may be, for example, activated carbon, silica, silica alumina, alumina, or zeolite. The catalyst may be used alone or in combination thereof. The most preferred catalyst is Raney nickel, which is economically advantageous. Raney nickel is usually developed with an alkali, so that, in particular, the pH of the reaction mixture should be monitored carefully. Because the reaction system is weakly alkaline, hydrolysis by the acidic aqueous solution is particularly effective for the deodorization.

The hydrogenation is typically conducted at from 50 to 200 degrees C. and from 1 to 100 MPa. The process of the hydrogenation may be batch-wise or continuous. In the batch-wise process, a reaction time depends on the amount of the catalyst and the temperature, and is usually 3 to 12 hours. A hydrogen pressure can be adjusted to a predetermined one as needed. A hydrogen pressure may be properly controlled to be constant. An end point of the hydrogenation is a time when a hydrogen pressure does not change, which is known by carefully watching a pressure gauge.

An aldehyde content in the organic group-modified organosilicone resin after purified in the acid treatment or the hydrogenation treatment may be 70 ppm or less, 20 ppm or less, or even 10 ppm or less.

The afore-mentioned two deodorizing treatments may be combined. The acid treatment may decompose an aldehyde compound, but cannot completely remove the unsaturated double bond and, therefore, cannot completely suppress generation of an aldehyde derived from the unsaturated double bond, which aldehyde is a cause of an odor. On the other hand, the hydrogenation may diminish the unsaturated double bond so as to reduce the amount of the aldehyde compound derived from the unsaturated double bond, but an aldehyde condensate formed by condensation of a part of the aldehyde remains in the system even after the hydrogenation treatment and cannot easily be removed by stripping. Then, complete deodorization is made by subjecting the addition reaction mixture to the hydrogenation to convert the remaining unsaturated double bond and, then, adding the acid catalyst to decompose the aldehyde condensate present in the system (Wo No. 2002/05588).

[Method for Preparing Hydrosilyl Group-Containing Organosilicone Resin as a Raw Material]

The hydrosilyl group-containing organosilicone resin represented by the average composition formula (13) may be either solid or liquid at 25 degrees C., but is preferably solid from the standpoint of a film-forming property. The resin is preferably diluted with an organic solvent from the standpoint of workability. A solvent having a boiling temperature higher than a reflux temperature in the hydrolysis is preferred.

Examples of the solvent used for the dilution include cyclic organopolysiloxanes such as octamethylcyclotetrasiloxane, decamethylcyclopentasiloxane, and dodecamethylcyclohexasiloxane; aromatic hydrocarbons such as toluene and xylene; ketone-based organic solvents such as acetone, methyl ethyl ketone, diethyl ketone, methyl isobutyl ketone; aliphatic hydrocarbons such as hexane, heptane, octane, and cyclohexane; and aliphatic alcohols such as methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol, and 1,2-propylene glycol. Octamethylcyclotetrasiloxane and decamethylcyclopentasiloxane are particularly preferred from the standpoint of storage stability and nonvolatility.

The hydrosilyl group-containing organosilicone resin represented by the average composition formula (13) may be prepared according to any known method, as described in Japanese Patent Application Laid-Open No. 2017-75283.

More specifically, the hydrosilyl group-containing organosilicone resin represented by the average composition formula (13) may be obtained by hydrolyzing, in the presence of an acid catalyst, a mixture of one or more selected from organosilicon compounds represented by the following formula (20) or (21), one or more selected from hydrosilyl group-containing organosilicon compounds represented by the following formula (22) or (23), and one or more selected from a hydrolyzable silane represented by the following formula (24), a partial hydrolysis condensate of the hydrolyzable silane and a metal salt of the hydrolyzable silane:

$$R^1{}_3SiOSiR^1{}_3 \quad (20)$$

$$R^1{}_3SiX^1 \quad (21)$$

$$H_pR^1{}_{(3-p)}SiOSiR^1{}_{(3-p)}H_p \quad (22)$$

$$H_pR^1{}_{(3-p)}SiX^2 \quad (23)$$

$$SiX^3{}_4 \quad (24)$$

wherein $R^1$ is as defined above, $X^1$, $X^2$ and $X^3$ are, independently of each other, a hydrolyzable functional group, and p is an integer of $1 \leq p \leq 3$, adding a basic catalyst in an amount larger than molar equivalent of the acid catalyst to neutralize the reaction mixture and, then, carrying out condensation in the presence of a basic catalyst.

In formulas (21), (23), and (24), $X^1$, $X^2$, and $X^3$ are, independently of each other, a hydrolyzable functional group each bonded directly to a silicon atom, such as halogen atoms such as chlorine and bromine, alkoxy groups such as methoxy, ethoxy, propoxy and butoxy, alkenoxy groups, acyloxy groups, amide groups, and oxime groups. Among these, a methoxy group, an ethoxy group and a chlorine atom are particularly preferred from the standpoint of availability and a hydrolysis rate.

Examples of the organosilicon compounds represented by the formula (20) include 1,1,1,3,3,3-hexamethyldisiloxane, 1,1,1,3,3,3-hexaphenyldisiloxane, 1,1,3,3-tetramethyl-1,3-divinyldisiloxane, 1,1,1,3,3,3-hexaethyldisiloxane, 1,1,1,3,3,3-hexavinyldisiloxane, 1,1,1,3,3-pentavinylmethyldisiloxane, 1,1,1,3,3-n-octylpentamethyldisiloxane, 1,1,1,3,3-chloromethylpentamethyldisiloxane, 1,1,3,3-tetramethyl-1,3-diallyldisiloxane, and 1,3-dimethyl-1,1,3,3-tetravinyldisiloxane. Particularly, 1,1,1,3,3,3-hexamethyldisiloxane and 1,1,1,3,3,3-hexaphenyldisiloxane are preferred.

Examples of the organosilicon compounds represented by the formula (21) include trimethylchlorosilane, triethylchlorosilane, ethyldimethylchlorosilane, trivinylchlorosilane, dimethylvinylchlorosilane, triphenylchlorosilane, dimethylphenylchlorosilane, methyldiphenylchlorosilane, trimethylmethoxysilane, trimethylethoxysilane, triethylmethoxysilane, triethylethoxysilane, triphenylmethoxysilane, and triphenylethoxysilane. Particularly, trimethylchlorosilane and trimethylthoxysilane are preferred.

Examples of the hydrosilyl group-containing organosilicon compounds represented by the formula (22) include 1,1,3,3-tetramethyldisiloxane and 1,1,1,3,3-pentamethyldisiloxane. Particularly, 1,1,3,3-tetramethyldisiloxane is preferred. It is noted that, while p in the formulas (22) and (23) is an integer satisfying the equation, $1 \leq p \leq 3$, p for H and $R^1$ bonded to one silicon atom and p for H and $R^1$ bonded to another silicon atom in the formula (22) may be the same or different from each other.

Examples of the hydrosilyl group-containing organosilicon compounds represented by the formula (23) include dimethylchlorosilane, diphenylchlorosilane, dimethylmethoxysilane, and dimethylethoxysilane. Particularly, dimethylchlorosilane and dimethylmethoxysilane are preferred.

Examples of the hydrolyzable silanes represented by the formula (24) include tetrachlorosilane, tetramethoxysilane, and tetraethoxysilane. Examples of the partial hydrolysis condensates of the hydrolyzable silane include tetramethoxysilane condensates and tetraethoxysilane condensates. Examples of the metal salts of the hydrolyzable silane include water glass, sodium silicate, and potassium silicate. Particularly, tetraethoxysilane and tetraethoxysilane condensates are preferred.

One or more selected from organosilicon compounds represented by the following formula (25) or (26) may be further added before the aforesaid hydrolysis of the mixture of compounds (20) to (24) in the presence of the acid catalyst, or after further hydrolysis, which will be described below, done before the aforesaid first hydrolysis, in the step of preparing the hydrosilyl group-containing organosilicone resin (13).

$$R^1SiX^4{}_3 \quad (25)$$

$$R^1{}_2SiX^5{}_2 \quad (26)$$

wherein $R^1$ is as defined above.

In the formulas (25) and (26), $X^4$ and $X^5$ are, independently of each other, a hydrolyzable functional group directly bonded to a silicon atom, such as halogen atoms such as chlorine and bromine atoms, alkoxy groups such as methoxy, ethoxy, propoxy and butoxy, alkenoxy groups, acyloxy groups, amide groups, and oxime groups. Among these, particularly, a methoxy group, an ethoxy group and a chlorine atom are preferred from the standpoints of availability and a hydrolysis rate.

Examples of the silicon compounds represented by the formula (25) include methyltrimethoxysilane, methyltriethoxysilane, ethyltrimethoxysilane, pentyltriethoxysilane, phenyltriethoxysilane, benzyltriethoxysilane, chloropropyltriethoxysilane, bromopropyltriethoxysilane, cyclohexyltrimethoxysilane, trifluoropropyltrimethoxysilane, and methyltrichlorosilane. Particularly, methyltrimethoxysilane, methyltriethoxysilane, and methyltrichlorosilane are preferred.

Examples of the silicon compounds represented by the formula (26) include dimethyldimethoxysilane, dimethyldiethoxysilane, diethyldimethoxysilane, dipentyldiethoxysilane, diphenyldiethoxysilane, dibenzyldiethoxysilane, dichloropropyldiethoxysilane, dibromopropyldiethoxysilane, dicyclohexyldimethoxysilane, difluoropropyldimethoxysilane, and dimethyldichlorosilane. Particularly, dimethyldimethoxysilane, dimethyldiethoxysilane, and dimethyldichlorosilane are preferred.

The method for preparing the hydrosilyl group-containing organosilicone resin represented by the average composition formula (13) will be described in further detail below.

In a reactor, are placed a solvent (particularly, organic solvent) and raw materials for hydrolysis (specifically, a mixture of one or more selected from the organosilicon compounds represented by the formula (20) or (21), one or more selected from the hydrosilyl group-containing organosilicon compounds represented by the formula (22) or (23), and one or more selected from the hydrolyzable silane represented by the formula (24), a partial hydrolysis condensate of the hydrolyzable silane and a metal salt of the hydrolyzable silane. Then, an acid is added as a catalyst and water is added dropwise, while stirring the mixture. Alternatively, the organic solvent may be added after completion of the dropwise addition of water. The addition of the acid catalyst is essential, because the hydrolysis is preferably carried out in an acidic condition.

The dropwise addition of water is conducted preferably at a temperature of from 0 to 80 degrees C., particularly preferably from 0 to 50 degrees C., whereby sudden rise of a temperature caused by the hydrolysis of the raw materials is avoided. An amount of water is such as t ogive a molar ratio of 0.6 to 2, preferably 1.0 to 1.8, relative to the hydrolyzable functional group (such as alkoxy group). Then, deactivation of the hydrosilyl group may be suppressed.

The solvent to be used in the hydrolysis is preferably an organic solvent in order to keep the reaction system homogeneous and suppress decrease in the reaction rate due to thickening during the hydrolysis. Further, a solvent having a boiling temperature higher than the reflux temperature during the hydrolysis is preferred.

Examples of the organic solvent include cyclic organopolysiloxanes such as octamethylcyclotetrasiloxane, decamethylcyclopentasiloxane, and dodecamethylcyclohexasiloxane; aromatic hydrocarbons such as toluene and xylene; ketone-based organic solvents such as acetone, methyl ethyl ketone, diethyl ketone, and methyl isobutyl ketone; and aliphatic hydrocarbons such as hexane, heptane, octane and cyclohexane.

In some cases, an alcohol solvent having 1 to 10 carbon atoms may be further added. Examples of the alcohol solvent include methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol, and 1,2-propylene glycol. Because the alcohol solvent does an alcohol exchange reaction with the hydrolyzable group such as an alkoxy group, a long-chain alcohol solvent may decrease a rate of the hydrolysis. Therefore, methanol, ethanol, 1-propanol and 2-propanol are particularly preferred.

An amount of the solvent is preferably from 1 to 80% by mass, particularly from 5 to 50% by mass, of the overall reaction mixture. Then, the reaction system is kept homogeneous, so that the reaction proceeds efficiently.

Examples of the acid catalyst include hydrochloric acid, sulfuric acid, sulfurous acid, fuming sulfuric acid, oxalic acid, p-toluenesulfonic acid, methanesulfonic acid, trifluoromethanesulfonic acid, phosphoric acid, formic acid, acetic acid, propionic acid, benzoic acid, and citric acid. The acid catalyst may be used in a small amount, preferably in a range of from 0.001 to 10% by mass of the overall reaction mixture.

After the dropwise addition of water, the reaction mixture is heated, for example, at a temperature of from 50 to 150 degrees C., more preferably from 80 to 120 degrees C., for about 2 to 8 hours to proceed with the hydrolysis. At this time, Here, deactivation of the hydrosilyl group may be further suppressed by conducting the reaction at a temperature lower than a boiling temperature of the hydrosilyl-containing organic compound used.

After the hydrolysis of the raw materials in the presence of the acid catalyst as described above, the reaction mixture is cooled down to a temperature of from 10 to 100 degrees C., preferably to from 10 to 60 degrees C., more preferably to from 10 to 30 degrees C., further preferably a temperature of 25 degrees C.

The hydrolysis is followed by neutralization with a basic catalyst such as alkali metal carbonates, alkali metal bicarbonates, and alkali metal hydroxides, at 10 to 40 degrees C. Co-use of a strongly basic catalyst and a weakly basic catalyst further facilitates suppression of the deactivation of the hydrosilyl group and the condensation of the organosilicone resin. Examples of the strongly basic catalyst include lithium hydroxide, sodium hydroxide, potassium hydroxide, calcium hydroxide, and barium hydroxide. Examples of the weakly basic catalyst include sodium carbonate, calcium carbonate and sodium bicarbonate. As the combination of the strongly basic catalyst and the weakly basic catalyst, a combination of sodium hydroxide and calcium carbonate is particularly preferred from the standpoint of easily increasing a molecular weight so as to obtain the hydrosilyl group-containing organosilicone resin having a high molecular weight.

An amount of the basic catalyst must be a molar equivalent larger than the molar equivalent of the acid catalyst. Neutralizing by such an amount of the basic catalyst preferentially promotes a condensation of the organosilicone resin to provide an increased molecular weight of the hydrosilyl group-containing organosilicone resin. The amount of the basic catalyst is preferably in a range of from 1.1 to 3.0 molar equivalents per molar equivalent of the acidic catalyst. Then, the condensation of the hydrosilyl group-containing organosilicone resin occurs preferentially to give a resin having an intended molecular weight.

After the neutralization, the alcohol generated, the solvent and excessive water may be removed by heating at from 95 to 120 degrees C. at normal pressure or a reduced pressure. After the removal of the alcohol, solvent and excessive water, a condensation is conducted by heating the residue at from 120 to 150 degrees C. for about 2 to 5 hours to thereby obtain the hydrosilyl group-containing organosilicone resin.

In the afore-mentioned method for preparing the hydrosilyl group-containing organosilicone resin, a ratio of a total of moles of the compounds of formulas (20), (21), (22), and (23) to moles of the $SiO_{4/2}$ unit of the compound of formula (24) is preferably from 0.3:1 to 2:1, more preferably from 0.6:1 to 1.3:1. A ratio of a total of moles of the compounds of the formulas (20) and (21) to a total of moles of the compounds of the formulas (22) and (23) is preferably from 0.3:1.0 to 2.0:1.0, more preferably from 0.6:1.0 to 1.3:1.0. Then, the amount of the hydrosilyl group contained in the hydrosilyl group-containing organosilicone resin is precisely quantitatively controlled. Thus, the amount of the hydrosilyl group contained in the organosilicone resin may be quantitatively changed in the present invention by changing the charged amounts of the compounds represented by the formulas (22) and (23).

In the method for preparing the hydrosilyl group-containing organosilicone resin, a deactivation of some of the hydrosilyl groups may occur as shown in the following reaction formula:

$$SiO_{1/2}H_{p'}R_{3-p'}\text{(M unit)}+\sim\text{Si-OH}\rightarrow\sim\text{Si—O—}SiO_{1/2}H_{p'-1}R_{3-p'} \quad \text{(D unit)}$$

wherein R is a monovalent hydrocarbon group having 1 to 10 carbon atoms and p' is an integer of from 1 to 3.

The deactivation of the hydrosilyl groups may be suppressed by dropwise adding one or more selected from the hydrosilyl group-containing organosilicon compounds represented by the formulas (22) or (23) to cause hydrolysis again, after the hydrolysis, in the presence of the acid catalyst, of a mixture of one or more selected from the organosilicon compounds represented the formulas (20) and (21) and one or more selected from the hydrolyzable silane represented by the formula (24), partial hydrolysis condensates of the hydrolyzable silane, and a metal salts of the hydrolyzable silanes.

The second hydrolysis is conducted preferably at a temperature lower than a boiling temperature of the hydrosilyl-containing organic compound, for example, at a temperature of from 40 to 150 degrees C., more preferably from 40 to 120 degrees C., for about 2 to 8 hours, whereby the deactivation of the hydrosilyl groups may be further suppressed. The deactivation of the hydrosilyl groups may be further suppressed by adjusting the amount of the raw materials or properly selecting the type of the catalyst.

The amount of hydrosilyl groups contained in the hydrosilyl group-containing organosilicone resin represented by the average composition formula (13) may be easily adjusted by changing a charged amount of the hydrosilyl group-containing organosilicon compound. This enables introduction of a large amount of the hydrosilyl group. Furthermore, a molecular weight distribution and structure may be controlled by changing the amounts of the raw materials for hydrolysis, the type and amount of the acidic catalyst, the reaction temperature, the reaction time, the amount of the solvent, or the addition manner, so that the hydrosilyl group-containing organosilicone resin suited for an intended use is provided.

[Physical Properties of the Crosslinked Organosilicone Resin]

The crosslinked organosilicone resin of the present invention has a weight average molecular weight of from 1,000 to 100,000, preferably from 3,000 to 500,000. Then, the resin is more preferred from the standpoint of performance and easy working such as filtration. It is to be noted that the weight average molecular weight may be determined as a polystyrene-reduced weight average molecular weight in gel permeation chromatography (GPC) (hereinafter, same).

The crosslinked organosilicone resin may be solid, gel-like or liquid at 25 degrees C., but preferably solid or gel-like, particularly preferably solid, from the standpoint of a film-forming property. Particularly, the crosslinked organosilicone resin of the average composition formula (1) in which a4 is an integer of $0 \leq a4 \leq 5$ and e in formula (2) is an integer of $0 < e \leq 20$ is preferred because it is solid at 25 degrees C. and has a weight average molecular weight of from 1,000 to 100,000, particularly, a weight average molecular weight of from 3,000 to 500,000 from the standpoint of performance and easy working such as filtration.

The crosslinked organosilicone resin having at least one of the groups represented by the aforesaid formula (2) or (3) is solid at 25 degrees C., so that it is suitable as a film-forming component. While an organosilicone resin before crosslinked forms a rigid film with brittleness, the crosslinked organosilicone resin forms a film which is less brittle, non-tacky, and flexible. This is because an organosilicone resin before crosslinked is cross-linked with flexible chains. In general, a hard film has low flexibility and a film with high flexibility tends to be soft. Thus, it has been generally considered that strength and flexibility of a film conflict with each other. However, the crosslinked organosilicone resin of the present invention forms a strong film, but the film is highly flexible and, accordingly, follows movement of a substrate.

Compared to a film of an organosilicone resin before crosslinked, the film of the crosslinked organosilicone resin has drastically improved resistance to an oil such as sebum. Non-crosslinked organosilicone resins tend to have improved oil resistance with an increased molecular weight. However, this improvement is limitative, because it is limitative to increase a molecular weight of non-crosslinked organosilicone resin. Thus, the improvement of the oil resistance is limitative. The crosslinking of an organosilicone resin with a crosslinking agent increases a molecular weight of the organosilicone resin in a sense to enhance the improvement of oil resistance. The crosslinked organosilicone resin of the present invention therefore has good oil resistance that cannot be achieved by conventional non-crosslinked organosilicone resins.

The crosslinked organosilicone resin of the present invention is preferably solid at 25 degrees C. and forms a film. Whether a material forms a film or not is judged as follows to see whether it forms a self-standing film when 1.5 grams of a 60% solution of the organosilicone resin in isododecane or decamethylcyclopentasiloxane is dropped on a PTFE (polytetrafluoroethylene resin) vessel and dried at 105 degrees C. for 3 hours to see if a self-standing film is formed. When it does not form a self-standing film, an oil oozes from through cracks of the film to show very bad oil resistance. The film is less capable to follow movement of a substrate, a cosmetic comprising the resin shows unnatural finish appearance.

A cosmetic comprising the resin as a film-forming component is not tacky when applied on the skin, is excellent in feeling in use, has good water resistance and oil resistance, and adheres intimately to the skin to show good makeup retention (durability).

An O/W emulsion of the crosslinked organosilicone resin of the present invention may be prepared and used as an intermediate composition for easy compounding in a water-based or an emulsion-based composition. Specifically, an O/W emulsion, as an intermediate composition, is prepared by dispersing a solution, in any oil, of the present crosslinked organosilicone resin into an aqueous continuous phase and is incorporated in a cosmetic. A manner of preparing the O/W emulsion is not particularly limited and may be any known method. For instance, one or more surface-active agents having an HLB of 10 or more may be used for emulsification. A surface-active agent having an HLB less than 10 an activator or a higher alcohol may be used a stabilizer. A carbomer may be incorporated in the aqueous phase for thickening.

[Cosmetics]

The crosslinked organosilicone resin (A) of the present invention may be used in a variety of applications, particularly as a raw material for cosmetics externally applied to the skin or hair. The amount of the crosslinked organosilicone resin (A) is preferably in a range of from 0.1 to 40 mass %, more preferably from 0.1 to 10 mass %, based on a whole mass of a cosmetic. Sufficient oil resistance is not attained below the lower limit of the amount. The feeling in use may be bad above the upper limit of the amount.

The crosslinked organosilicone resin (A) of the present invention may also be provided in a dissolved form which is obtained by dissolving the resin in any oil. When the oil is volatile, the oil evaporates from the solution to form a film. Thus, the dissolved-form of the product works as a film-forming component.

(B) Volatile Oil

Volatile oils having a boiling temperature of 240 degrees C. or less are preferred in consideration that a film is formed from the resin and exhibits its effect soon after application of the cosmetic. Particularly, silicone oils, isododecane, and ethanol are preferred. These may be combined, depending on a type of a base material of a cosmetic. For example, when the base material of a cosmetic is of a silicone type, a silicone oil may be proper to improve the compatibility of the whole composition of a cosmetic. A silicone oil will provide a good feeling in touch. Examples of commercially available silicone oil include TMF-1.5, KF-995, KF-96L-1cs, KF-96L-1.5cs, and KF-96L-2cs (all ex. Shin-Etsu Chemical Co., Ltd).

[Other Components]

The cosmetics of the present invention may comprise other various components usually used in cosmetics. Examples of the other components include (C) oils other than component (B), (D) powder, (E) surfactants, (F) cross-linked organopolysiloxanes, (G) film-forming components other than (A), (H) aqueous components, and (1) other additives. They may be used either alone or in combination of two or more as needed. These components may be selected and used, depending on the type of cosmetics. The amounts of these components may be such as usual as known for the type of cosmetics.

(C) Oil

The cosmetics of the present invention may comprise (C) an oil other than component (B). The oil may be solid, semi-solid or liquid at room temperature as long as it has a boiling temperature higher than 240 degrees C. Examples of the oil include silicone oils, natural animal and plant oils and fats, semi-synthetic oils and fats, hydrocarbon oils, higher alcohols, fatty acids, ester oils, fluorinated oils, and ultraviolet absorbers. When the oil is compounded, the amount of the oil is preferably from 1 to 95 mass %, more preferably from 15 to 40 mass %, based on the overall cosmetic, though not particularly limited thereto.

Silicone Oil

A silicone oil is not particularly limited as long as it is usually compounded in cosmetics. Specific examples of the silicone oil include linear or branched organopolysiloxanes having low to high viscosities, such as dimethylpolysiloxane, dodecamethylcyclohexasiloxane, caprylylmethicone, methylphenylpolysiloxane, methylhexylpolysiloxane, methyl hydrogen polysiloxane, and dimethylsiloxane-methylphenylsiloxane copolymers and amino-modified organopolysiloxanes. Among these, particularly preferred are low-viscosity silicones (such as KF-96A-6cs; commercially available product of Shin-Etsu Chemical Co., Ltd.) which give a fresh feeling in use, phenyl silicones (such as KF-56A and 54HV; commercially available products of Shin-Etsu Chemical Co., Ltd.) used for the purpose of improving compatibility with other oils or lustering, and silicone waxes (such as KP-561P, 562P, and KF-70205; commercially available products of Shin-Etsu Chemical Co., Ltd.) used for the purpose of lustering or adjusting a feeling in use. These silicone oils may be used either alone or in combination of two or more.

Examples of the natural animal and plant oils and fats and semisynthetic oils and fats include avocado oil, linseed oil, almond oil, insect wax, perilla oil, olive oil, cacao butter, kapok wax, kaya nut oil, carnauba wax, liver oil, candelilla wax, beef tallow, neat's foot oil, neat's bone oil, hardened beef tallow, apricot kernel oil, whale oil, hardened oil, wheat germ oil, sesame oil, rice germ oil, rice barn oil, sugarcane wax, sasanqua oil, safflower oil, shea butter, china wool oil, cinnamon oil, jojoba wax, squalene, shellac wax, turtle oil, soybean oil, tea seed oil, camellia oil, evening primrose oil, corn oil, lard, rapeseed oil, Japanese tung oil, rice bran wax, germ oil, horse tallow, persic oil, palm oil, palm kernel oil, castor oil, hydrogenated castor oil, castor oil fatty acid methyl ester, sunflower oil, grape seed oil, bayberry wax, jojoba oil, macadamia nut oil, bees wax, mink oil, cottonseed oil, cotton wax, Japanese wax, Japanese wax kernel oil, montan wax, coconut oil, hardened coconut oil, coconut fatty acid triglyceride, mutton tallow, peanut oil, lanolin, liquid lanolin, reduced lanolin, lanolin alcohol, hard lanolin, lanolin acetate, lanolin fatty acid isopropyl, POE lanolin alcohol ether, POE lanolin alcohol acetate, lanolin fatty acid polyethylene glycol, POE hydrogenated lanolin alcohol ether, and egg yolk oil, wherein "POE" means polyoxyethylene.

Examples of the hydrocarbon oil include isohexadecane, ozokerite, squalane, squalene, ceresin, paraffin, paraffin wax, polyethylene wax, polyethylene-polypropylene wax, liquid paraffin, pristane, polyisobutylene, microcrystalline wax, and vaseline. Examples of the higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of the higher alcohol oil include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol), and monooleyl glyceryl ether (selachyl alcohol).

Examples of the ester oil include diisobutyl adipate, 2-hexyldecyl adipate, di-2-heptylundecyl adipate, isononyl isononanoate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprylate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearylate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate. Examples of the glyceride oil include acetoglyceryl, glyceryl triisooctanoate, glyceryl triisostearate, glyceryl triisopalmitate, glyceryl monostearate, glyceryl di-2-heptylundecanoate, glyceryl trimyristate, and diglyceryl myristate/isostearate.

Examples of the fluorinated oil include perfluoropolyether, perfluorodecalin, and perfluorooctane.

Examples of the ultraviolet absorber include homomenthyl salicylate, octocrylene, 4-tert-butyl-4'-methoxydibenzoylmethane, 4-(2-β-glucopyranosyloxy) propoxy-2-hydroxybenzophenone, octyl salicylate, hexyl 2-[4-(diethylamino)-2-hydroxybenzoyl]benzoate, dihydroxydimethoxybenzophenone, sodium dihydroxydimethoxybenzophenone disulfonate, dihydroxybenzophenone, dimethicodiethylbenzalmalonate, 1-(3,4-dimethoxyphenyl)-4,4-dimethyl-1,3-pentanedione, 2-ethylhexyl dimethoxybenzylidene dioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methylbis(trimethylsiloxy)silylisopentyl trimethoxycinnamate, drometrizole trisiloxane, 2-ethylhexyl paradimethylaminobenzoate, isopropyl paramethoxycinnamate, 2-ethylhexyl paramethoxycinnamate, 2,4-bis-[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenonesulfonic acid and trihydrate thereof, sodium hydroxymethoxybenzophenonesulfonate, phenylbenzimidazolesulfonic acid, and 2,2'-methylenebis[6-(2H-benzotriazol-2-yl)-4-(1,1,3,3-tetramethylbutyl)phenol]. Further, a UVA absorber (for example, hexyl diethylamino hydroxybenzoyl benzoate) and a UVB absorber (for example, ethylhexyl methoxycinnamate) may be used in combination and each of them may be properly combined.

A component having high compatibility with component (A) of the present invention is preferable as the oil (C) in order to easily compound component (A) in a cosmetic. However, a component having low compatibility may be sometimes preferred in a low amount or for some application, because it makes component (A) to exhibit its film performance. That is, component (A) is phase-separated, using an oil having low compatibility therewith, to attain a film effect. Specifically, there is provided a cosmetic product wherein component (A) is dispersed, using the volatile oil (B) as a compatibilizer, in a phase (x) comprising a colorant and an oil having low compatibility. When the cosmetic is applied, the volatile oil (B) in the disperse phase evaporates cause phase separation between the phase (x) and component (A) on the skin or lip, so that a film phase comprising component (A) is separated from phase (x) comprising a colorant, and secondary adhesion is prevented. Examples of the oil having low compatibility include hydrogenated polyisobutenes having a high molecular weight and highly polymerized phenyl silicones. Alternatively, in a case of a wax-comprising cosmetic, a cosmetic composition is heated at a high temperature to melt component (A) and, if any, optional components and then cooled to lower the compatibility to obtain a cosmetic so that a phase comprising component (A) and the optional components is dispersed in a phase (y) comprising a wax. When the cosmetic is applied, the phase comprising component (A) and the optional components is formed in a surface of the applied cosmetic membrane to exhibit a film performance, as mentioned above.

(D) Powder

Powder is not particularly limited as long as it may be compounded in a cosmetic. Examples of the powder include pigments and silicone spherical powder. An amount of the powder is preferably from 0.1 to 90 mass %, more preferably from 1 to 35 mass %, of the overall cosmetic, though not particularly limited thereto.

The pigment is not particularly limited as long as it is usually used in makeup cosmetics. Examples of the pigment include inorganic pigments such as talc, mica, cericite, synthetic phlogopite, barium sulfate, aluminum oxide, kaolin, silica, calcium carbonate, zinc oxide, titanium oxide, red iron oxide, yellow iron oxide, black iron oxide, ultramarine, Prussian blue, carbon black, Substoichiometric Titanium Oxide, cobalt violet, chromium oxide, chromium hydroxide, cobalt titanate, bismuth oxychloride, and titanium-mica pearl pigment; organic pigments such as zirconium-, barium- or aluminum lake-based ones including Pigment Red 201, Red 202, Red 204, Red 205, Red 220, Red 226, Red 228, Red 405, Orange 203, Yellow 205, Yellow 4, Yellow 5, Blue 1, Blue 404, and Green 3; natural coloring matters such as chlorophyll and 0-carotene; and dyes.

The powder may be surface-treated. A surface treating agent is preferably such capable of providing the powder with hydrophobicity in order not to damage the water resistance of the product. The surface treating agent is not particularly limited as long as it can provide the powder with hydrophobicity. Examples of the surface treating agent include surface-treat silicone agents, waxes, paraffins, organofluorine compounds of a perfluoroalkyl and a phosphate, surfactants, amino acids such as N-acylglutamic acid, aluminum stearate, and metal soaps such as magnesium myristate. More preferred are surface-treating silicone agents such as silanes and silylating agents such as caprylsilane (AES-3083, product of Shin-Etsu Chemical Co., Ltd.) and trimethoxysilyl dimethicone; silicone oils such as dimethyl silicone (KF-96A series; product of Shin-Etsu Chemical Co., Ltd.), methyl hydrogen polysiloxane (KF-99P, KF-9901, etc.; product of Shin-Etsu Chemical Co., Ltd.), a silicone branched type silicone treatment agent (KF-9908, KF-9909, etc.; product of Shin-Etsu Chemical Co., Ltd.); and acrylic silicone (KP-574, KP-541; product of Shin-Etsu Chemical Co., Ltd.). The above-described surface hydrophobization agents may be used either alone or in combination of two or more. Examples of a surface-treated coloring pigment include KTP-09 series; products of Shin-Etsu Chemical Co., Ltd., particularly, KTP-09W, 09R, 09Y and 09B. Examples of a dispersion containing hydrophobized superfine titanium oxide or hydrophobized superfine zinc oxide include SPD-T5, T6, T7, T5L, Z5, Z6, and Z5L; all ex. Shin-Etsu Chemical Co., Ltd. A content of these in a cosmetic is preferably from 0.01 to 95 mass %.

Examples of spherical silicone powder include crosslinked silicone powder (i.e., so-called silicone rubber powder composed of an organopolysiloxane having a crosslinked structure in which repeating chains of diorganosiloxane units have been crosslinked), silicone resin particles (polyorganosilsesquioxane resin particles having a three-dimensional network structure), and silicone resin-coated silicone rubber powder. Specific examples of the crosslinked silicone powder and the silicone resin particles are known by the name of (dimethicone/vinyl dimethicone) cross polymer, and polymethylsilsesquioxane. They are commercially available in a powder form or as swollen product containing a silicone oil, and are commercially available in the trade name of, for example, KMP-598, 590, 591, or KSG-016F (all ex. Shin-Etsu Chemical Co., Ltd.). Due to the rolling effect peculiar to spherical powder, these powder can provide the resulting cosmetic with slipperiness and improved feeling in use. They may be used either alone or in combination of two or more.

The silicone resin-coated silicone rubber powder is preferred particularly because of its effects for improving touch by preventing tackiness and for reducing unevenness such as wrinkles or pores of the skin. Specific examples of the silicone resin-coated silicone rubber powder include those defined by the Japanese Labeling Name of Cosmetic Components, such as (vinyl dimethicone/methicone silsesquioxane) cross polymer, (diphenyl dimethicone/vinyl diphenyl dimethicone/silsesquioxane) cross polymer, polysilicone-22, and polysilicone-1 cross polymer. They are commercially available in the trade names, KSP-100, 101, 102, 105, 300, 411, and 441 (all ex. Shin-Etsu Chemical Co., Ltd.).

These powders may be used either alone or in combination of two or more. Its content in a cosmetic is preferably from 0.01 to 95 mass %.

(E) Surfactant

Examples of the surfactant or surface-active agent include nonionic, anionic, cationic, and amphoteric ones as long as they are used in common cosmetics. They may be used either alone or in combination of two or more as needed. Among these surfactants, ones which are preferred from the standpoint of compatibility with the oil containing the component (A) are crosslinked polyether-modified silicones, crosslinked polyglycerin-modified silicones, linear or branched polyoxyethylene-modified organopolysiloxanes, linear or branched polyoxyethylene polyoxypropylene-modified organopolysiloxanes, linear or branched polyoxyethylene/alkyl-co-modified organopolysiloxanes, linear or branched polyoxyethylene polyoxypropylene/alkyl co-modified organopolysiloxanes, linear or branched polyglycerin-modified organopolysiloxane, and linear or branched polyglycerin/alkyl co-modified organopolysiloxanes. In these surfactants, the content of a hydrophilic polyoxyethylene group, polyoxyethylene polyoxypropylene group or polyglycerin residue accounts preferably for from 10 to 70% of the molecule. Specific examples of such include KSG-210, 240, 310, 320, 330, 340, 320Z, 350Z, 710, 810, 820, 830, 840, 820Z, 850Z, KF-6011, 6013, 6017, 6043, 6028, 6038, 6048, 6100, 6104, 6105, and 6106 (all ex. Shin-Etsu Chemical Co., Ltd.). Its content in a cosmetic is preferably from 0.01 to 15 mass %.

(F) Crosslinked Organopolysiloxane

Any crosslinked organopolysiloxane commonly used in cosmetics may be used without limitation. They may be used either alone or in combination of two or more as needed. This crosslinked organopolysiloxane is not spherical, unlike the silicone powder described in (D) above. In addition, this does not have a polyether or polyglycerin structure in a molecular structure, unlike the surfactant (E). This is an elastomer that swells with an oil to show a structural viscosity. Specific examples of this include (dimethicone/vinyl dimethicone) crosspolymer, (dimethicone/phenyl vinyl dimethicone) crosspolymer, (vinyl dimethicone/lauryl dimethicone) crosspolymer, and (lauryl polydimethylsiloxyethyl dimethicone/bisvinyl dimethicone) crosspolymer, as defined by the Japanese Labeling Name of Cosmetic Components. They are commercially available as a swollen product containing an oil which is liquid at room temperature. Specific examples include KSG-15, 1510, 16, 1610, 18A, 19, 41A, 42A, 43, 44, 042Z, 045Z, and 048Z (all ex. Shin-Etsu Chemical Co., Ltd.). Its amount in a cosmetic is preferably from 0.01 to 30 mass % as a solid content.

(G) Film-Forming Component Other than (A)

An existing film-forming component may be incorporated together as long as it does not impair the effects of the present invention. Any existing film-forming component may be such that are compounded in common cosmetics. Specific examples of such include latexes such as polyvinyl alcohol, polyvinylpyrrolidone, polyvinyl acetate, and poly (alkyl acrylate), dextrin, cellulose derivatives such as alkyl cellulose and nitrocellulose, silicone-modified polysaccharide compounds such as tri(trimethylsiloxy)silylpropylcarbamic acid pullulan, acrylic silicone-based graft copolymers such as (alkyl acrylate/dimethicone) copolymers, silicone-based resins such as trimethylsiloxysilicic acid, silicone-based resins such as silicone-modified polynorbornene and fluorine-modified silicone resins, fluorine resins, aromatic hydrocarbon resins, polymer emulsion resins, terpene-based resins, polybutene, polyisoprene, alkyd resins, polyvinylpyrrolidone-modified polymers, rosin-modified resins, and polyurethane.

Among these, silicone-based film-forming components are particularly preferred, such as, tri(trimethylsiloxy)silylpropylcarbamic acid pullulans [TSPL-30-D5, ID; commercially available product of Shin-Etsu Chemical Co., Ltd., as dissolved in a solvent], (alkyl acrylate/dimethicone) copolymers [KP-543, 545, 549, 550, or 545L; commercially available product of Shin-Etsu Chemical Co., Ltd., as dissolved in a solvent], trimethylsiloxysilicates [KF-7312J, X-21-5250; commercially available product of Shin-Etsu Chemical Co., Ltd., as dissolved in a solvent], silicone-modified polynorbornenes [NBN-30-ID; commercially available product of Shin-Etsu Chemical Co., Ltd., as dissolved in a solvent], and organosiloxane graft polyvinyl alcohol-based polymers, though not limited thereto. In particular, a combination of tri(trimethylsiloxy)silylpropylcarbamic acid pullulan with the component (A) offers effects of spinnability and thickening to provides a stronger film. A combination of an (alkyl acrylate/dimethicone) copolymer with component (A) provides a more flexible film. A combination of trimethylsiloxysilicic acid with component (A) provides a stronger film. The existing film-forming components other than component (A) may be used either alone or in combination of two or more. Its content in a cosmetic is preferably from 0.1 to 20 mass %.

(H) Aqueous Component

An aqueous component is not particularly limited as long as it may be compounded in common cosmetics. Specific examples of the aqueous component include humectants such as water, lower alcohols, sugar alcohols such as erythritol, maltitol, xylitol, and sorbitol, and polyhydric alcohols such as 1,3-BG, glycerin, PG, and DPG. They may be used either alone or in combination of two or more as needed. Its content in a cosmetic is preferably from 0.1 to 90 mass %.

(I) Other Additives

Examples of the other additives include oil-soluble gelling agents, water-soluble thickeners, antiperspirants, antiseptics/bactericides, perfumes, salts, antioxidants, pH adjusters, chelating agents, refreshing agents, anti-inflammatory agents, skin care agents (whitening agents, cell activators, skin roughness improving agents, blood flow stimulants, skin astringents, antiseborrheic agents, etc.), vitamins, amino acids, water-soluble polymer compounds, fibers, and clathrate compounds.

Oil-Soluble Gelling Agent

Examples of the oil-soluble gelling agent include metal soaps such as aluminum stearate, magnesium stearate, and zinc myristate; amino acid derivatives such as N-lauroyl-L-glutamic acid and $\alpha$, $\gamma$-di-n-butylamine; dextrin fatty acid esters such as dextrin palmitate, dextrin stearate, and dextrin 2-ethylhexanoate/palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organo-modified clay minerals such as disteardimonium hectorite, stearalkonium hectorite, and hectorite.

Water-Soluble Thickener

Examples of the water-soluble thickener include plant-based polymers such as gum arabic, tragacanth, galactan, carob gum, guar gum, karaya gum, carrageenan, pectin, agar, quince seed (marmelo), starch (rice, corn, potato, wheat, and the like), alge colloid, tranto gum, and locust bean gum; microbial polymers such as xanthan gum, dextran, succinoglucan, and pullulan; animal-based polymers such as collagen, casein, albumin, and gelatin; starch-based polymers such as carboxymethyl starch, and methylhydroxypropyl starch; cellulose-based polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose, cationized cellulose, and powdery cellulose; alginic acid-based polymers such as sodium alginate and propylene glycol alginate; vinyl-based polymers such as polyvinyl methyl ether and carboxyvinyl polymer; polyoxyethylene-based polymers; polyoxyethylene polyoxypropylene copolymer-based polymers; acrylic polymers such as sodium polyacrylate, poly(ethyl acrylate), polyacrylamide, and acryloyldimethyltaurate copolymer; other synthetic water-soluble polymers such as polyethyleneimines and cationic polymers; and inorganic water-soluble polymers such as bentonite, aluminum magnesium silicate, montmorillonite, beidellite, nontronite, saponite, hectorite, and silicic anhydride.

Among these, one or more of the water-soluble thickeners selected from the plant-based polymers, microbial polymers, animal-based polymers, starch-based polymers, cellulose-based polymers, alginic acid-based polymers, polyoxyethylene polyoxypropylene copolymer-based polymers, acrylic polymers, and inorganic water-soluble polymers are preferred.

Antiperspirant

Examples of the antiperspirant include aluminum hydroxy halides such as aluminum chlorohydrate and aluminum chlorohydroxy allantoinate, aluminum halides such as aluminum chloride, allantoin aluminum salt, tannic acid, persimmon tannin, aluminum potassium sulfate, zinc oxide, zinc paraphenol sulfonate, burnt alum, tetrachloro (Al)/zirconium) hydrate, and trichlorohydrex glycine (Al/zirconium). In particular, aluminum hydroxyhalides, aluminum halides, and complexes or mixtures between them and a zirconyl oxyhalide or zirconyl hydroxyhalide (for example, tetrachloro (Al/zirconium)hydrate and trichlorohydrex glycine (Al/zirconium)) are preferred as a component providing a high effect.

Antiseptic/Bactericide

Examples of the antiseptic/bactericide include alkyl paraoxybenzoates, benzoic acid, sodium benzoate, sorbic acid, potassium sorbate, phenoxyethanol, imidazolidinylurea, salicylic acid, isopropyl methyl phenol, carbolic acid, parachlorometacresol, hexachlorophene, benzalkonium chloride, chlorohexidine chloride, trichlorocarbanilide, iodopropynyl butylcarbamate, polylysine, photosensitizers, silver, and plant extracts.

Perfume

Examples of the perfume include natural perfumes and synthetic perfumes. Examples of the natural perfumes include plant perfumes separated from flowers, leaves, lumber, skins, and the like and animal perfumes such as musk and civet. Examples of the synthetic perfumes include hydrocarbons such as monoterpenes, alcohols such as aliphatic alcohols and aromatic alcohols, aldehydes such as terpene aldehydes and aromatic aldehydes, ketones such as alicyclic ketones, esters such as terpene esters, lactones, phenols, oxides, nitrogenous compounds, and acetals.

Salts

Examples of the salts include inorganic salts, organic acid salts, amine salts and amino acid salts. Examples of the inorganic salts include sodium salts, potassium salts, magnesium salts, calcium salts, aluminum salts, zirconium salts, and zinc salts of an inorganic acid such as hydrochloric acid, sulfuric acid, carbonic acid, or nitric acid. Examples of the organic acid salts include salts of an organic acid such as acetic acid, dehydroacetic acid, citric acid, malic acid, succinic acid, ascorbic acid, or stearic acid. Examples of the amine salts and amino acid salts include salts of an amine such as triethanolamine and salts of an amino acid such as glutamic acid. In addition, salts of hyaluronic acid, chondroitin sulfuric acid, or the like, and further, acid-alkali neutralization salts used in the formulation may also be used.

Antioxidant

The antioxidant is not particularly limited, and include carotenoids, ascorbic acid and salts thereof, ascorbyl stearate, tocophenol, tocophenol acetate, tocopherol, p-t-butylphenol, butylhydroxyanisole, dibutylhydroxytoluene, phytic acid, ferulic acid, thiotaurine, hypotaurine, sulfites, erythorbic acid and salts thereof, chlorogenic acid, epicatechin, epigallocatechin, epigallocatechin gallate, apigenin, kaempferol, myricetin, and quercetin.

pH Adjuster

Examples of the pH adjuster include lactic acid, citric acid, glycolic acid, succinic acid, tartaric acid, dl-malic acid, potassium carbonate, sodium bicarbonate, and ammonium bicarbonate.

Chelating Agent

Examples of the chelating agent include alanine, sodium edetate, sodium polyphosphate, sodium metaphosphate, and phosphoric acid.

Refreshing Agent

Examples of the refreshing agent include L-menthol, camphor, and menthyl lactate.

Anti-Inflammatory Agent

Examples of the anti-inflammatory agent include allantoin, glycyrrhizinic acid and salts thereof, glycyrrhetinic acid, stearyl glycyrrhetinate, tranexamic acid, and azulene.

Skin Care Agent

Examples of the skin care agent include whitening agents such as placenta extract, albutin, glutathione, and saxifraga sarmentosa extract, cell activators such as royal jelly, photosensitizer, cholesterol derivative, deproteinized calf blood extract, skin roughness improving agents, blood flow stimulants such as nonanoic vanillylamide, benzyl nicotinate, β-butoxyethyl nicotinate, capsaicin, zingerone, cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthine, and 7-oryzanol, skin astringents, and antiseborrheic agents such as sulfur and thiantrol.

Vitamins

Examples of the vitamins include vitamins A such as vitamin A oil, retinol, retinol acetate, and retinol palmitate, vitamins B such as vitamins $B_2$, e.g., riboflavin, riboflavin butyrate, and flavinadenine nucleotide, vitamins $B_6$, e.g., pyridoxine hydrochloride, pyridoxine dioctanoate, and pyridoxine tripalmitate, vitamin $B_{12}$ and derivatives thereof, and vitamin B15 and derivatives thereof, vitamins C such as L-ascorbic acid, L-ascorbyl dipalmitate, sodium L-ascorbyl-2-sulfate, and dipotassium L-ascorbyl phosphate, vitamins D such as ergocalciferol and cholecalciferol, vitamins E such as α-tocopherol, β-tocopherol, γ-tocopherol, dl-α-tocopherol acetate, dl-α-tocopherol nicotinate, and dl-α-tocopherol succinate, nicotinic acids such as nicotinic acid, benzyl nicotinate, and nicotinic amide, vitamin H, vitamin P, pantothenoic acids such as calcium pantothenate, D-pantothenyl alcohol, pantothenyl ethyl ether, and acetylpantothenyl ethyl ether, and biotin.

Amino Acids

Examples of the amino acids include glycine, valine, leucine, isoleucine, serine, threonine, phenylalanine, arginine, lysine, aspartic acid, glutamic acid, cystine, cysteine, methionine, and tryptophan.

Nucleic Acid

Examples of the nucleic acid include deoxyribonucleic acid.

Hormone

Examples of the hormone include estradiol and ethenyl estradiol.

Clathrate Compounds

Examples of the clathrate compound include cyclodextrin.

The cosmetics may be either an emulsion one or a nonaqueous one. An emulsion type is selected for providing the skin with a fresh feeling in use and it may be any of an O/W emulsion, W/O emulsion, O/W/O emulsion, and W/O/W emulsion. A nonaqueous composition or powder composition may be selected for providing the skin with an oily feel or water resistance. In either case, a good cosmetic is obtained. It is noted that the term "nonaqueous composition" as used herein means that water is not intentionally incorporated. Among these, a nonaqueous composition is particularly preferred because high oil resistance may be expected.

The crosslinked organosilicone resin of the present invention may be compounded by various methods to prepare a cosmetic. For example, the resin may be dissolved in component (B) in advance, which solution is then dried up with a spray dryer to obtain a solid which is easily resolved, or which solution is incorporated in an O/W emulsion and is used in a cosmetic.

The cosmetic of the present invention may be facial essence, milky lotion, cream, hair care, foundation, premakeup, sunscreen, concealer, blush color, lip stick, gloss, balm, mascara, eye shadow, eye liner, body makeup, deodorant, and nail care cosmetics, though not restricted to those. Among these, makeup cosmetics such as foundation, lip stick, mascara, and eye liner and cosmetics having a sunscreen effect are preferred. Appearance of the cosmetic of the present invention may be various, such as liquid, cream, solid, paste, gel, mousse, souffle, clay, powder, and stick.

EXAMPLES

The present invention will hereinafter be described in further detail by the Examples and the Comparative Examples, but the present invention is not limited to the Examples.

Hereinafter, "%" means mass %, unless otherwise specified.

The hydrosilyl group-containing organosilicone resin used below as a raw material is synthesized in accordance with the preparation method described in Japanese Patent Application Laid-Open No. 2017-75283.

Example 1

Method for Preparing a Solution of 60% of a Crosslinked Organosilicone Resin in Decamethylcyclopentasiloxane In a reactor, were placed 1,000 g of a 50% solution of a powdery hydrosilyl group-containing organosilicone resin (weight average molecular weight: 4,430, hydrogen gas generation: 9.1 mL/g) and represented by the following average composition formula (E1) in decamethylcyclopentasiloxane, 98.6 g of organopolysiloxane having a vinyl group at both ends and represented by the following formula (E2), 1,000 g of 2-propanol, and 0.6 g of a 0.5% solution of chloroplatinic acid in 2-propanol and heated at 80 degrees C. for 6 hours to cause reaction. Then, the solvent was distilled off by heating at a reduced pressure. Further, after addition of 250 g of ethanol, 5 g of a 5% aqueous solution of sodium hydroxide was added to hydrolyze unreacted hydrosilyl groups. Concentrated hydrochloric acid (0.63 g) was then added to neutralize the reaction mixture. The reaction mixture was heated at a reduced pressure to distill off ethanol, followed by filtration to obtain a solution of a crosslinked organosilicone resin represented by the following formula (E3) in decamethylcyclopentasiloxane.

The solution thus obtained was heated at 120 to 130 degrees C. at a reduced pressure to thereby remove decamethylcyclopentasiloxane to obtain a powder (weight average molecular weight: 156,000).

$$(Me_3SiO_{1/2})_{26.5}(HMe_2SiO_{1/2})_{1.8}(SiO_2)_{36.0}$$ Formula (E1):

Formula (E2)

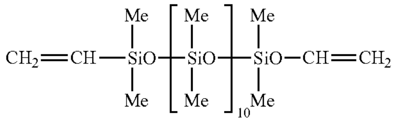

$$(Me_3SiO_{1/2})_{26.5}(X_{1/2}Me_2SiO_{1/2})_{1.8}(SiO_2)_{36}$$ Formula (E3):

wherein

X =

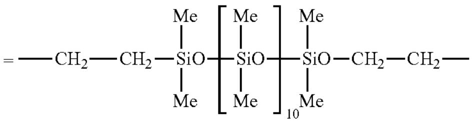

wherein Me is a methyl group, hereinafter the same, and a part of X in the formula (E3) may be a hydroxyl group.

Example 2

Method for Preparing a Solution of 60% of a Crosslinked Organosilicone Resin in Decamethylcyclopentasiloxane In a reactor, were placed 1,300 g of a 50% solution of a powdery hydrosilyl group-containing organosilicone resin (weight average molecular weight: 4,480, hydrogen gas generation: 8.0 mL/g) and represented by the following average composition formula (E4) in decamethylcyclopentasiloxane, 80.6 g of organopolysiloxane having a vinyl group at both ends and represented by the following formula (E5), 1,300 g of 2-propanol, and 0.7 g of a 0.5% solution of chloroplatinic acid in 2-propanol and heated at 100 degrees C. for 6 hours to cause reaction. Then, 223.0 g of a polyoxyalkylene represented by the following formula (E6) was added to the mixture and the reaction was continued by heating at 100 degrees C. for 6 hours and, then, the solvent was distilled off by further heating at a reduced pressure. Further, after addition of 325 g of ethanol, 6.5 g of a 5% aqueous solution of sodium hydroxide was added to the mixture to hydrolyze unreacted hydrosilyl groups. Concentrated hydrochloric acid (0.8 g) was then added to neutralize the reaction mixture. After neutralization, 195 g of a 0.01N aqueous solution of hydrochloric acid was added to hydrolyze the allyl ether groups of the unreacted polyoxyalkylene, followed by neutralization with 3.3 g of a 5% aqueous solution of sodium bicarbonate. After the reaction mixture was transferred to an autoclave, 50 g of Raney nickel was added and the reaction was conducted at 100 degrees C. for 3 hours while introducing hydrogen at a hydrogen pressure of 1 MPa. The reaction mixture was heated at a reduced pressure to distill off ethanol, followed by filtration to obtain a solution of a crosslinked organosilicone resin represented by the following average composition formula (E7) in decamethylcyclopentasiloxane.

The solution thus obtained was heated at 120 to 130 degrees C. at a reduced pressure to thereby remove decamethylcyclopentasiloxane to obtain a powder (weight average molecular weight: 45,600).

$(Me_3SiO_{1/2})_{33.0}(HMe_2SiO_{1/2})_{5.6}(SiO_2)_{48.0}$ Formula (E4):

Formula (E5)

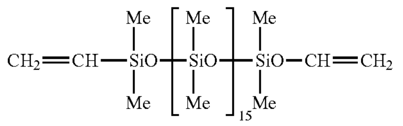

$CH_2{=}CH{-}CH_2{-}O{-}(C_2H_4O)_9{-}H$ Formula (E6):

$(Me_3SiO_{1/2})_{33.0}(X_{1/2}Me_2SiO_{1/2})_{1.1}(R^2Me_2SiO_{1/2})_{4.5}(SiO_2)_{48.0}$ Formula (E7):

wherein

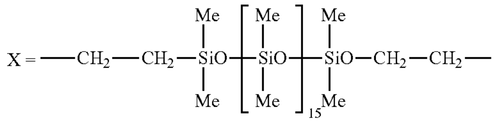

$R^2{=}{-}CH_2{-}CH_2{-}CH_2{-}O{-}(C_2H_4O)_9{-}H$

In the formula (E7), a part of $R^2$ and X may be a hydroxyl group.

Example 3

Method for Preparing a Solution of 60% of a Crosslinked Organosilicone Resin in Decamethylcyclopentasiloxane In a reactor, were placed 900 g of a 50% solution of a powdery hydrosilyl group-containing organosilicone resin (weight average molecular weight: 5,030, hydrogen gas generation: 15.1 mL/g) and represented by the following average composition formula (E8) in decamethylcyclopentasiloxane, 59.8 g of organopolysiloxane having a vinyl group at both ends represented by the following formula (E9), 900 g of 2-propanol, and 0.6 g of a 0.5% solution of chloroplatinic acid in 2-propanol and heated at 95 degrees C. for 6 hours to cause reaction. Then, 100.0 g of organopolysiloxane represented by the following formula (E10) was added and the reaction was continued by heating the resulting mixture at 100 degrees C. for 6 hours, the solvent was distilled off by further heating at a reduced pressure. Then, after addition of 225 g of ethanol, 4.5 g of a 5% aqueous solution of sodium hydroxide was added to hydrolyze unreacted hydrosilyl groups. Concentrated hydrochloric acid (0.6 g) was then added to neutralize the reaction mixture. The reaction mixture was then heated at a reduced pressure to distill off the ethanol, followed by filtration to obtain a solution of a crosslinked organosilicone resin represented by the following average composition formula (E11) in decamethylcyclopentasiloxane.

The solution thus obtained was heated at 120 to 130 degrees C. at a reduced pressure to thereby remove decamethylcyclopentasiloxane to obtain a powder (weight average molecular weight: 32,400).

$(Me_3SiO_{1/2})_{25.0}(HMe_2SiO_{1/2})_{3.4}(Me_2SiO)_{10.0}(SiO_2)_{34.0}$ Formula (E8):

Formula (E9)

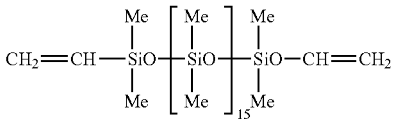

$CH_2{=}CH{-}(SiO(CH_3)_2)_5{-}Si(CH_3)_3$ Formula (E10):

$(Me_3SiO_{1/2})_{25.0}(X_{1/2}Me_2SiO_{1/2})_{1.0}(R^3Me_2SiO_{1/2})_{2.4}(Me_2SiO)_{10.0}(SiO_2)_{34.0}$ Formula (E11):

wherein

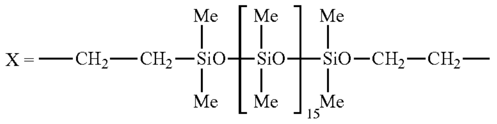

$R^3{=}{-}CH_2{-}CH_2{-}(SiO(CH_3)_2)_5{-}Si(CH_3)_3$

In the formula (E11), a part of $R^3$ and X may be a hydroxyl group.

Example 4

Method for Preparing a Solution of 60% of a Crosslinked Organosilicone Resin in Decamethylcyclopentasiloxane In a reactor, were placed 1,100 g of a 50% solution of a solid hydrosilyl group-containing organosilicone resin (weight average molecular weight: 9,860, hydrogen gas generation: 24.5 mL/g) and represented by the following average composition formula (E12) in decamethylcyclopentasiloxane, 101.4 g of organopolysiloxane having a vinyl group at both ends and represented by the following formula (E13), 1,100 g of 2-propanol, and 0.8 g of a 0.5% solution of chloroplatinic acid in 2-propanol and heated at 85 degrees C. for 6 hours to cause reaction. Then, 135.0 g of a polyglycerin represented by the following formula (E14) was added and the reaction was continued by heating at 100 degrees C. for 6 hours, the solvent was distilled off by further heating at a reduced pressure. Further, after addition of 275 g of ethanol, 5.5 g of a 5% aqueous solution of sodium hydroxide was added to hydrolyze unreacted hydrosilyl groups. Concentrated hydrochloric acid (0.7 g) was then added to neutralize the reaction mixture. After neutralization, 165 g of a 0.01N aqueous solution of hydrochloric acid was added to hydrolyze the allyl ether groups of the unreacted polyglycerin, followed by neutralization with 2.8 g of a 5% aqueous solution of sodium bicarbonate. The reaction mixture was heated at a reduced pressure to distill off ethanol, followed by filtration. The residue was diluted with decamethylcyclopentasiloxane so that the weight percentage of the crosslinked organosilicone resin was 60% and a solution of 60% of a crosslinked organosilicone resin represented by the following average composition formula (E15) in decamethylcyclopentasiloxane was obtained.

The solution thus obtained was heated at 120 to 130 degrees C. at a reduced pressure to thereby remove decamethylcyclopentasiloxane to obtain a powder (weight average molecular weight: 267,000).

$(Me_3SiO_{1/2})_{52.0}(HMe_2SiO_{1/2})_{10.8}(SiO_2)_{82.0}$ Formula (E12):

Formula (E13)

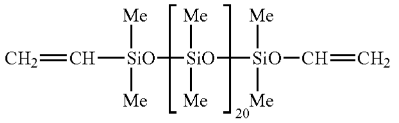

$CH_2{=}CH{-}CH_2{-}O{-}(CH_2(OH)CH_2O)_3{-}H$ Formula (E14):

$(Me_3O_{12})_{52.0}(X_{1/2}Me_2SiO_{1/2})_{2.2}(R^2Me_2SiO_{1/2})_{8.6}(SiO_2)_{82.0}$ Formula (E15):

wherein

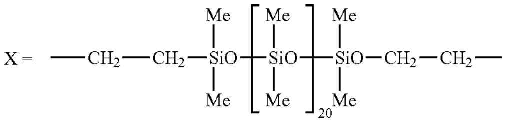

$R^2{=}{-}CH_2{-}CH_2{-}CH_2{-}O{-}(CH_2CH(OH)CH_2O)_3{-}H$

In the formula (E15), a part of $R^2$ and X may be a hydroxyl group.

Example 5

Method for Preparing a Solution of 60% of a Crosslinked Organosilicone Resin in Decamethylcyclopentasiloxane In a reactor, were placed 800 g of a 50% solution of a solid hydrosilyl group-containing organosilicone resin (weight average molecular weight: 5,940, hydrogen gas generation: 8.3 mL/g) and represented by the following average composition formula (E15) in decamethylcyclopentasiloxane, 234.1 g of an organopolysiloxane having a vinyl group at both ends and represented by the following formula (E16), 800 g of 2-propanol, and 0.6 g of a 0.5% solution of chloroplatinic acid in 2-propanol and heated at 105 degrees C. for 6 hours to cause reaction. Then, the solvent was distilled off by heating at a reduced pressure. Further, after addition of 200 g of ethanol, 4.0 g of a 5% aqueous solution of sodium hydroxide was added to hydrolyze unreacted hydrosilyl groups. Concentrated hydrochloric acid (0.5 g) was then added to neutralize the reaction mixture. The reaction mixture was heated at a reduced pressure to distill off ethanol, followed by filtration to obtain a solution of a crosslinked organosilicone resin represented by the following average composition formula (E17) in decamethylcyclopentasiloxane.

The solution thus obtained was heated at 120 to 130 degrees C. at a reduced pressure to thereby remove decamethylcyclopentasiloxane to obtain a gel form product (weight average molecular weight: 335,000).

$(Me_3SiO_{1/2})_{36.0}(HMe_2SiO_{1/2})_{2.2}(SiO_2)_{48.0}$ Formula (E15):

Formula (E16)

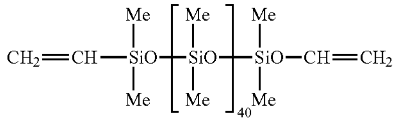

$(Me_3SiO_{1/2})_{36.0}(X_{1/2}Me_2SiO_{1/2})_{2.2}(SiO_2)_{48.0}$ Formula (E17):

wherein

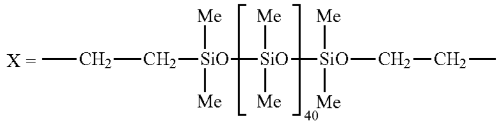

In the formula (E17), a part of X may be a hydroxyl group.

Example 6

Method for Preparing a Solution of 60% of a Crosslinked Organosilicone Resin in Decamethylcyclopentasiloxane In a reactor, were placed 800 g of a 50% solution of a solid hydrosilyl group-containing organosilicone resin (weight average molecular weight: 5,940, hydrogen gas generation: 8.3 mL/g) and represented by an average composition formula (E18) in decamethylcyclopentasiloxane, 343.7 g of organopolysiloxane having a vinyl group at both ends and represented by the following formula (E19), 800 g of 2-propanol, and 0.7 g of a 0.5% solution of chloroplatinic acid in 2-propanol and heated at 105 degrees C. for 6 hours to cause reaction. Then, the solvent was distilled off by heating at a reduced pressure. Further, after addition of 200 g of ethanol, 4.0 g of a 5% aqueous solution of sodium hydroxide was added to hydrolyze unreacted hydrosilyl groups. Concentrated hydrochloric acid (0.5 g) was then added to neutralize the reaction mixture. The reaction mixture was heated at a reduced pressure to distill off ethanol, followed by filtration to obtain a solution of a crosslinked organosilicone resin represented by the following average composition formula (E20) in decamethylcyclopentasiloxane.

The solution thus obtained was heated at 120 to 130 degrees C. at a reduced pressure to thereby remove decamethylcyclopentasiloxane to obtain a gel form product (weight average molecular weight: 488,000).

$(Me_3SiO_{1/2})_{36.0}(HMe_2SiO_{1/2})_{2.2}(SiO_2)_{48.0}$ Formula (E18):

Formula (E19)

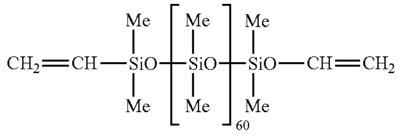

$(Me_3SiO_{1/2})_{36.0}(X_{1/2}Me_2SiO_{1/2})_{2.2}(SiO_2)_{48.0}$ Formula (E20):

wherein

X = 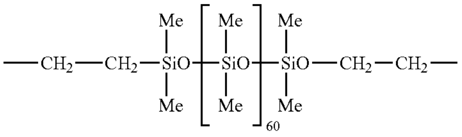

In the formula (E20), a part of X may be a hydroxyl group.

Example 7

Method for Preparing a Solution of 60% of a Crosslinked Organosilicone Resin in Decamethylcyclopentasiloxane In a reactor, were placed 800 g of a 50% solution of a solid hydrosilyl group-containing organosilicone resin (weight average molecular weight: 5,940, hydrogen gas generation: 8.3 mL/g) and represented by the following average composition formula (E21) in decamethylcyclopentasiloxane, 67.9 g of organopolysiloxane having a vinyl group at both ends and represented by the following formula (E22), 221.3 g of organopolysiloxane represented by the following formula (E23) and having a vinyl group at both ends, 800 g of 2-propanol, and 0.7 g of a 0.5% solution of chloroplatinic acid in 2-propanol and heated at 105 degrees C. for 6 hours to cause reaction. Then, the solvent was distilled off by heating at a reduced pressure. Further, after addition of 200 g of ethanol, 4.0 g of a 5% aqueous solution of sodium hydroxide was added to hydrolyze unreacted hydrosilyl groups. Concentrated hydrochloric acid (0.5 g) was then added to neutralize the reaction mixture. The reaction mixture was heated at a reduced pressure to distill off ethanol, followed by filtration to obtain a solution of a crosslinked organosilicone resin represented by the following average composition formula (E24) in decamethylcyclopentasiloxane.

The solution thus obtained was heated at 120 to 130 degrees C. at a reduced pressure to thereby remove decamethylcyclopentasiloxane to obtain a solid (weight average molecular weight: 221,000).

$(Me_3SiO_{1/2})_{36.0}(HMe_2SiO_{1/2})_{2.2}(SiO_2)_{48.0}$ Formula (E21):

Formula (E22)

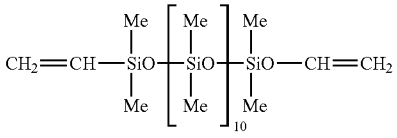

Formula (E23)

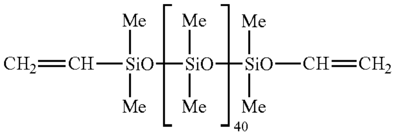

$(Me_3SiO_{1/2})_{36.0}(X_{1/2}Me_2SiO_{1/2})_{1.1}(R^4{}_{1/2}Me_2SiO_{1/2})_{1.1}(SiO_2)_{48.0}$ Average composition formula (E24):

wherein

X = 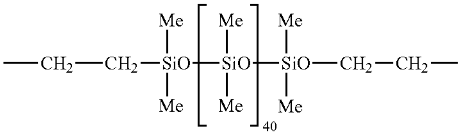

$R^4$ = 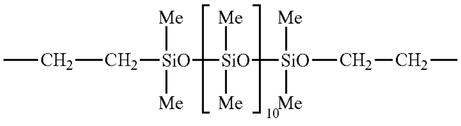

In the formula (E24), a part of $R^4$ and X may be a hydroxyl group.

Example 8

Method for Preparing a Solution of 60% of a Crosslinked Organosilicone Resin in Decamethylcyclopentasiloxane In a reactor, were placed 1,300 g of a 50% solution of a powdery hydrosilyl group-containing organosilicone resin (weight average molecular weight: 8,550, hydrogen gas generation: 10.0 mL/g) and represented by the following average composition formula (E25) in decamethylcyclopentasiloxane, 40.8 g of organopolysiloxane having a vinyl group at both ends and represented by the following formula (E26), 1,300 g of 2-propanol, and 0.8 g of a 0.5% solution of chloroplatinic acid in 2-propanol and heated at 100 degrees C. for 6 hours to cause reaction. Then, 82.7 g of a polyoxyalkylene represented by the following formula (E27) was added and the reaction was continued by heating at 100 degrees C. for 6 hours, the solvent was distilled off by further heating at a reduced pressure. Further, after addition of 325 g of ethanol, 6.5 g of a 5% aqueous solution of sodium hydroxide was added to hydrolyze unreacted hydrosilyl groups. Concentrated hydrochloric acid (0.8 g) was then added to neutralize the reaction mixture. After neutralization, 195 g of a 0.01N aqueous solution of hydrochloric acid was added to hydrolyze the allyl ether group of the unreacted polyoxyalkylene, followed by neutralization with 3.3 g of a 5% aqueous solution of sodium bicarbonate. After the reaction mixture was transferred to an autoclave, 50 g of Raney nickel was added and a reaction was conducted for 3 hours at 100 degrees C. while introducing hydrogen at a hydrogen pressure of 1 MPa. The reaction mixture was heated at a reduced pressure to distill off the solvent, followed by filtration to obtain a solution of a crosslinked organosilicone resin represented by the following average composition formula (E28) in decamethylcyclopentasiloxane.

The solution thus obtained was heated at 120 to 130 degrees C. at a reduced pressure to thereby remove decamethylcyclopentasiloxane to obtain a powder (weight average molecular weight: 63,800).

$(Me_3SiO_{1/2})_{52.0}(HMe_2SiO_{1/2})_{3.8}(SiO_2)_{68.0}$ Formula (E25):

Formula (E26)

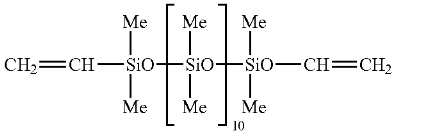

$CH_2=CH-CH_2-O-(C_2H_4O)_5(C_3H_6O)_2-CH_3$ Formula (E27):

$(Me_3SiO_{1/2})_{52.0}(X_{1/2}Me_2SiO_{1/2})_{1.1}(R^2Me_2SiO_{1/2})_{2.7}(SiO_2)_{68.0}$ Formula (E28):

wherein

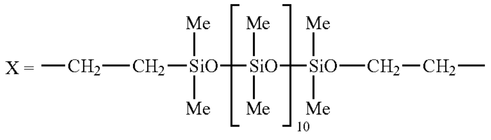

$R^2=-CH_2-CH_2-CH_2-O-(C_2H_4O)_5(C_3H_6O)_2-CH_3$ Formula (E28):

In the formula (E28), a part of $R^2$ and X may be a hydroxyl group.

Example 9

Method for Preparing a Solution of 60% of a Crosslinked Organosilicone Resin in Decamethylcyclopentasiloxane In a reactor, were placed 800 g of a 50% solution of a solid hydrosilyl group-containing organosilicone resin (weight average molecular weight: 5,940, hydrogen gas generation: 8.3 mL/g) and represented by the following average composition formula (E29) in decamethylcyclopentasiloxane, 67.9 g of organopolysiloxane represented by the following formula (E30) and having a vinyl group at both ends, 7.5 g of a hydrocarbon represented by the following formula (E31) and having a vinyl group at both ends, 800 g of 2-propanol, and 0.7 g of a 0.5% solution of chloroplatinic acid in 2-propanol and heated at 105 degrees C. for 6 hours to cause reaction. Then, the solvent was distilled off by heating at a reduced pressure. Further, after addition of 200 g of ethanol, 4.0 g of a 5% aqueous solution of sodium hydroxide was added to hydrolyze unreacted hydrosilyl groups. Concentrated hydrochloric acid (0.5 g) was then added to neutralize the reaction mixture. The reaction mixture was heated at a reduced pressure to distill off the solvent, followed by filtration to obtain a solution of a crosslinked organosilicone resin represented by the following average composition formula (E32) in decamethylcyclopentasiloxane.

The solution thus obtained was heated at 120 to 130 degrees C. at a reduced pressure to thereby remove decamethylcyclopentasiloxane to obtain a solid (weight average molecular weight: 221,000).

$(Me_3SiO_{1/2})_{36.0}(HMe_2SiO_{1/2})_{2.2}(SiO_2)_{48.0}$ Formula (E29):

Formula (E30)

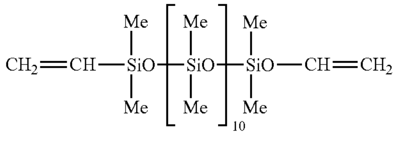

$CH_2=CH-(CH_2)_4-CH=CH_2$ Formula (E31):

$(Me_3SiO_{1/2})_{36.0}(X_{1/2}Me_2SiO_{1/2})_{1.1}(R^4{}_{1/2}Me_2SiO_{1/2})_{1.1}(SiO_2)_{48.0}$ Formula (E32):

wherein

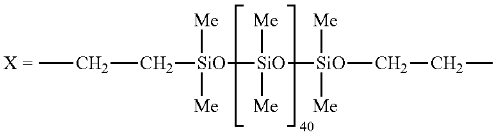

$R^4=-CH_2-CH_2-(CH_2)_4-CH_2-CH_2-$

In the formula (E32), a part of $R^4$ and X may be a hydroxyl group.

Comparative Example 1

Method for Preparing a Solution of 60% of a Non-Crosslinked Organosilicone Resin in Decamethylcyclopentasiloxane In a reactor, were placed 80 g (0.49 mol) of hexamethyldisiloxane, 180 g of ethyl polysilicate having a $SiO_2$ content of 40 mass % (a $SiO_2$ content in ethyl polysilicate was 1.2 mol*) and 80 g of isopropanol. Methanesulfonic acid (1.2 g, 12.5 mmol) was further added and the resulting mixture was cooled to from 10 to 20 degrees C. While stirring, 42.6 g (2.36 mol) of water was added dropwise. After completion of the dropwise addition, the reaction mixture was heated at 70 to 90 degrees C. for 6 hours to be hydrolized. After completion of the hydrolysis, the hydrolyzate was cooled to room temperature and 1.92 g (12.0 mmol) of a 25 wt % aqueous solution of sodium hydroxide and 0.25 g (2.5 mmol) of calcium carbonate were added to neutralize the acid. Then, 140 g of decamethylcyclopentasiloxane was added and the resulting mixture was heated to 120 degrees C. to remove ethanol, isopropanol, and excess water generated by the hydrolysis. After confirmation of completely removing the solvent, the residue was heated at 150 degrees C. for 5 hours. Further, the reaction mixture was diluted with decamethylcyclopentasiloxane and then, filtered to obtain 320 g of a solution of 50% of a non-crosslinked organosilicone resin in decamethylcyclopentasiloxane (weight average molecular weight: 6,300).

Comparative Example 2

Method for Preparing a Solution of 60% of a Non-Crosslinked Organosilicone Resin in Decamethylcyclopentasiloxane In a reactor, were placed 151.34 g (0.68 mol) of hexamethyldisiloxane, 333.8 g (1.87 mol) of methyltriethoxysilane, 245.7 g of ethyl polysilicate having a $SiO_2$ content of 40 mass % (a $SiO_2$ content in ethyl polysilicate was 1.64 mol*) and 250 g of isopropanol. Methanesulfonic acid (6.0 g, 62.4 mmol) was further added and the resulting mixture was cooled to from 10 to 20 degrees C. While stirring, 194.7 g (10.8 mol) of water was added dropwise. After completion of the dropwise addition, the reaction mixture was heated at 70 to 90 degrees C. for 6 hours to be hydrolysed. After completion of the hydrolysis, the hydrolyzate was cooled to room temperature and the acid was neutralized by adding 9.6 g (60.0 mmol) of a 25 wt % aqueous solution of sodium hydroxide and 1.25 g (12.4 mmol) of calcium carbonate. Then, 140 g of decamethylcyclopentasiloxane was added and the resulting mixture was heated to 120 degrees C. to remove ethanol, isopropanol, and excess water generated by the hydrolysis. After confirmation of completely removing the solvent, the residue was heated at 150 degrees C. for 5 hours. Further, the reaction mixture was diluted with decamethylcyclopentasiloxane and then filtered to obtain 650 g of a solution of 50% of a non-crosslinked organosilicone resin in decamethylcyclopentasiloxane (weight average molecular weight: 8,200).

*In Comparative Examples 1 and 2, the mol of $SiO_2$ in ethyl polysilicate is calculated from a total mass of ethyl polysilicate.

For example, in 180 g of ethyl polysilicate having a $SiO_2$ content (Mw=60) of 40 mass %, an amount of Q ($SiO_2$) unit=180×0.4/60=1.2 (mol).

The state, film-forming ability and continuity, hardness and flexibility of a film of each of the organosilicone resins obtained in the Examples and the Comparative Examples were evaluated at 25 degrees C., as described below. The results are shown in Table 1.

1) The solution of the product in decamethylcyclopentasiloxane obtained in the Example or the Comparative Example was heated at 120 to 130 degrees C. at a reduced pressure to thereby remove decamethylcyclopentasiloxane so as to obtain the organosilicone resin. The state of the organosilicone resin obtained was observed at 25 degrees C.

2) 1.5 Grams of the solution containing 60% of the organosilicone resin and the solvent were put dropwise in a vessel of PTFE and dried at 105° C. for 3 hours to obtain a film. When the film was self-standing, a film-forming ability was evaluated as good.

3) When the film obtained in 2) above did not have cracks, the film continuity was evaluated as good.

4) When the film obtained in 2) above allowed a nail to penetrate therein, the film was evaluated as soft.

5) A film was obtained as in 2) above with the exception that a laboratory dish made of aluminum was used instead of the vessel of PTFE. When the film was bent without breaking, flexibility of the film was evaluated as good. When the film broke, its flexibility was evaluated as poor.

TABLE 1

| | Form | Film forming ability | Film continuity | Film hardness | Flexibility |
|---|---|---|---|---|---|
| Example 1 | Solid | Good | Good | Hard | Good |
| Example 2 | Solid | Good | Good | Hard | Good |
| Example 3 | Solid | Good | Good | Soft | Good |
| Example 4 | Solid | Good | Good | Soft | Good |
| Example 5 | Gel | Good | Good | Soft | Good |
| Example 6 | Gel | Good | Good | Soft | Good |
| Example 7 | Solid | Good | Good | Hard | Good |
| Example 8 | Solid | Good | Good | Hard | Good |
| Example 9 | Solid | Good | Good | Hard | Good |
| Comparative Example 1 | Solid | Good | Poor | Hard | Poor |
| Comparative Example 2 | Solid | Good | Good | Hard | Poor |

The films obtained in Examples 1 to 8 were all uniform, continuous, non-tacky, and non-brittle. When they were bent, they showed high flexibility. The film obtained in Comparative Example 1 was composed of a non-crosslinked organosilicone resin having M and Q units. It was not tacky, but was hard and had cracks. It was easily broken by bending. The film obtained in Comparative Example 2 was composed of a non-crosslinked organosilicone resin having M, T, and Q units. It was not tacky and was uniform and continuous, but was broken by bending to show low flexibility. The introduction of the T unit in the skeleton of the organosilicone resin improved brittleness, but flexibility was not improved. The crosslinked organosilicone resins of the present invention had greatly improved flexibility, compared to the conventional non-crosslinked organosilicone resins.

3 Microliters of each of squalane, oleic acid and triethylhexanoin were dropped each on the films obtained in Examples 1 to 8 and Comparative Examples 1 and 2 to measure a contact angle. The results are shown in the following table.

TABLE 2

| Contact Angle, ° | Squalane | Oleic Acid | Triethylhexanoin |
|---|---|---|---|
| Example 1 | 49.3 | 51.5 | 52.0 |
| Example 2 | 43.0 | 44.0 | 46.7 |
| Example 3 | 48.5 | 50.1 | 49.3 |
| Example 4 | 50.0 | 51.6 | 51.4 |
| Example 5 | 40.3 | 42.1 | 42.6 |
| Example 6 | 39.8 | 40.8 | 41.1 |
| Example 7 | 46.5 | 47.3 | 45.8 |
| Example 8 | 41.1 | 42.2 | 42.6 |
| Comparative Example 1 | 26.7 | 12.5 | 11.8 |
| Comparative Example 2 | 25.4 | 11.9 | 10.2 |

The films obtained in Examples 1 to 8 had a large contact angle with all of the oils: squalane, oleic acid, and triethylhexanoin and, thus, had a high oil resistance. The films obtained in Comparative Examples 1 and 2 had, on the other hand, a low contact angle with all of the oils and, thus, had a low oil resistance. Non-crosslinked organosilicone resins tend to have improved oil resistance with an increased molecular weight. However, this improvement is limitative, because it is limitative to increase a molecular weight of non-crosslinked organosilicone resin. Thus, the improvement of the oil resistance is limitative. The crosslinking of an organosilicone resin with a crosslinking agent increases a molecular weight of the organosilicone resin in a sense to enhance the improvement of oil resistance. The crosslinked organosilicone resin of the present invention therefore has good oil resistance that cannot be achieved by conventional non-crosslinked organosilicone resins.

Example 10

Method for Preparing a Solution of 60% of a Crosslinked Organosilicone Resin Dissolved in Isododecane In a reactor, were placed 1,000 g of a 50% solution of a powdery hydrosilyl group-containing organosilicone resin (weight average molecular weight: 4,430, hydrogen gas generation: 9.1 mL/g) and represented by the following average composition formula (E1) in isododecane, 98.6 g of organopolysiloxane represented by the following formula (E2) and having a vinyl group at both ends, 1,000 g of 2-propanol, and 0.6 g of a 0.5% solution of chloroplatinic acid in 2-propanol and heated at 80 degrees C. for 6 hours to cause reaction. Then, the solvent was distilled off by heating at a reduced pressure. Further, after addition of 250 g of ethanol, 5 g of a 5% aqueous solution of sodium hydroxide was added to hydrolyze unreacted hydrosilyl groups. Concentrated hydrochloric acid (0.63 g) was then added to neutralize the reaction mixture. The reaction mixture was heated at a reduced pressure to distill off the solvent, followed by filtration to obtain a solution of a crosslinked organosilicone resin in isododecane.

The solution thus obtained was heated at 120 to 130 degrees C. at a reduced pressure to thereby remove isododecane to obtain a powder.

$$(Me_3SiO_{1/2})_{26.5}(HMe_2SiO_{1/2})_{1.8}(SiO_2)_{36.0} \quad \text{Formula (E1):}$$

Formula (E2)

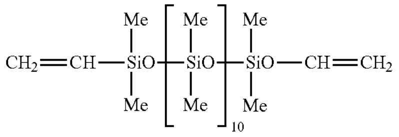

$$(Me_3SiO_{1/2})_{26.5}(X_{1/2}Me_2SiO_{1/2})_{1.8}(SiO_2)_{36} \quad \text{Formula (E3):}$$

wherein

X =

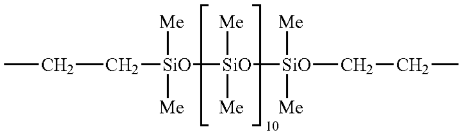

In the formula (E3), a part of X may be a hydroxyl group.

Example 11

Method for Preparing a Solution of 60% of a Crosslinked Organosilicone Resin Dissolved in Methyl Trimethicone In a reactor, were placed 1,000 g of a 50% solution of a powdery hydrosilyl group-containing organosilicone resin (weight average molecular weight: 4,430, hydrogen gas generation: 9.1 mL/g) and represented by the following average composition formula (E1) in methyl trimethicone, 98.6 g of organopolysiloxane represented by the following formula (E2) and having a vinyl group at both ends, 1,000 g of 2-propanol, and 0.6 g of a 0.5% solution of chloroplatinic acid in 2-propanol and heated at 80 degrees C. for 6 hours to cause reaction. Then, the solvent was distilled off by heating at a reduced pressure. Further, after addition of 250 g of ethanol, 5 g of a 5% aqueous solution of sodium hydroxide was added to hydrolyze unreacted hydrosilyl groups. Concentrated hydrochloric acid (0.63 g) was then added to neutralize the reaction mixture. The reaction mixture was heated at a reduced pressure to distill off ethanol, followed by filtration to obtain a solution of a crosslinked organosilicone resin in methyl trimethicone.

The solution thus obtained was heated at 120 to 130 degrees C. at a reduced pressure to thereby remove methyl trimethicone to obtain a powder.

$$(Me_3SiO_{1/2})_{26.5}(HMe_2SiO_{1/2})_{1.8}(SiO_2)_{36.0} \quad \text{Formula (E1):}$$

Formula (E2)

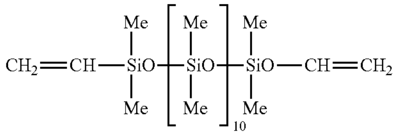

$$(Me_3SiO_{1/2})_{26.5}(X_{1/2}Me_2SiO_{1/2})_{1.8}(SiO_2)_{36} \quad \text{Formula (E3):}$$

wherein

X =

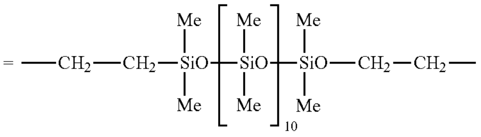

In the formula (E3), a part of X may be a hydroxyl group.

The polymers thus obtained are soluble not also in D5, isododecane, or methyl trimethicone but also in a silicone, such as dimethicone (2cs or 6cs), usable for cosmetics, triethylhexanoin, or an ester oil such as isotridecyl isononanoate. The viscosity of solutions thus available can be changed by the composition or molecular weight of the polymers.

Examples 12 and 13 and Comparative Examples 3 and 4

Emulsion type cream foundations having the composition shown below in Table 3 were prepared.

TABLE 3

| | | Example | | Comparative Example | |
|---|---|---|---|---|---|
| Number | Component, mass % | 12 | 13 | 3 | 4 |
| 1 | Crosslinked polyether-modified silicone (Note 1) | 4.0 | ditto | ditto | ditto |
| 2 | Crosslinked dimethylpolysiloxane (Note 2) | 6.0 | ditto | ditto | ditto |
| 3 | Polyether-modified silicone (Note 3) | 2.0 | ditto | ditto | ditto |
| 4 | Dimethylpolysiloxane (Note 4) | 2.0 | ditto | ditto | ditto |
| 5 | Decamethylcyclopentasiloxane | 6.3 | ditto | ditto | ditto |
| 6 | Triethylhexanoin | 4.0 | ditto | ditto | ditto |
| 7 | Neopentyl glycol dioctanoate | 2.0 | ditto | ditto | ditto |
| 8 | Polymethylsilsesquioxane powder (Note 5) | 1.5 | ditto | ditto | ditto |
| 9 | 1,3-BG | 5.0 | ditto | ditto | ditto |
| 10 | Sodium chloride | 0.5 | ditto | ditto | ditto |
| 11 | Water | 50.8 | ditto | ditto | ditto |
| 12 | Silicone-treated titanium oxide (Note 6) | 8.7 | ditto | ditto | ditto |
| 13 | Silicone-treated red iron oxide (Note 6) | 0.45 | ditto | ditto | ditto |
| 14 | Silicone-treated yellow iron oxide (Note 6) | 0.75 | ditto | ditto | ditto |
| 15 | Silicone-treated black iron oxide (Note 6) | 0.10 | ditto | ditto | ditto |
| 16 | Dissolved product (60% solution) of Example 1 | 5.0 | — | — | — |
| 17 | Dissolved product (60% solution) of Example 7 | — | 5.0 | — | — |
| 18 | Dissolved product (60% solution) of Comparative Example 1 | — | — | 5.0 | — |
| 19 | Dissolved product (60% solution) of Comparative Example 2 | — | — | — | 5.0 |
| 20 | Antioxidant | 0.5 | ditto | ditto | ditto |

TABLE 3-continued

| Number | Component, mass % | Example 12 | Example 13 | Comparative Example 3 | Comparative Example 4 |
|---|---|---|---|---|---|
| 21 | Antiseptic | 0.2 | ditto | ditto | ditto |
| 22 | Perfume | 0.2 | ditto | ditto | ditto |
| Total | | 100 | ditto | ditto | ditto |

(Note 1)
KSG-210; product of Shin-Etsu Chemical Co., Ltd.
(Note 2)
KSG-15; product of Shin-Etsu Chemical Co., Ltd.
(Note 3)
KF-6017; product of Shin-Etsu Chemical Co., Ltd.
(Note 4)
KF-96A-6cs; product of Shin-Etsu Chemical Co., Ltd.
(Note 5)
KMP-590; product of Shin-Etsu Chemical Co., Ltd.
(Note 6)
KTP-09W, R, Y, B; product of Shin-Etsu Chemical Co., Ltd.

<Preparation of a Cosmetic>

A: Components 1 to 5, 7, 8, and 16 to 20 were mixed uniformly.

B: Components 12 to 15 were dispersed in component 6 with a three-roll mill and added to A, followed by uniform mixing.

C: Components 9 to 11 and 21 were mixed uniformly.

D: C was added to B, and the resulting mixture was emulsified, to which Component 22 was then added to obtain an emulsion type cream foundation.

The emulsion type cream foundation was evaluated as follows.

[Evaluation of Usability]

The emulsion type cream foundations thus obtained were evaluated by a panel of 10 female experts on spreadability, tackiness, uneven color in finish and makeup retention (endurance at 8 hours after application) according to the following criteria.

[Secondary Adhesion]

The emulsion type cream foundations were each applied on the forehead of the experts. Twenty minutes after the application, tissue paper was pressed against the place to which the foundation was applied and, then, secondary adhesion of the cosmetic was evaluated according to the following criteria.

TABLE 4

| Evaluation score | Spreadability | Tackiness | Uneven color | Makeup retention | Secondary adhesion |
|---|---|---|---|---|---|
| 5 | Excellent | None | None | Excellent | None |
| 4 | Good | Almost None | Almost None | Good | Almost None |
| 3 | Moderate | Moderate | Moderate | Moderate | Moderate |
| 2 | Poor | A little sticky | A little unevenness | Poor | Poor |
| 1 | Worst | Sticky | Unevenness | Untransparent | Worst |

The scores given by the ten experts were averaged and ranked as follows.

A: average of 4.0 or more

B: average of 3.0 or more and less than 4.0

C: average of 2.0 or more and less than 3.0

D: average of less than 2.0

TABLE 5

| Evaluation | Example 12 | Example 13 | Comparative Example 3 | Comparative Example 4 |
|---|---|---|---|---|
| Spreadability | A | B | C | D |
| Tackiness | A | A | C | B |
| Uneven color | A | A | B | C |
| Makeup retention | A | A | C | C |
| Secondary adhesion | A | A | D | C |

As seen from Table 5, the cosmetics of the present invention were markedly superior to those of Comparative Examples 3 and 4 in the spreadability, makeup retention, and secondary adhesion.

Examples 14 and 15 and Comparative Example 5

Lip sticks having the composition shown below in Table 6 were prepared.

TABLE 6

| Component Number | Component, mass % | Example 14 | Example 15 | Comparative Example 5 |
|---|---|---|---|---|
| 1 | *Candelilla* wax | 4.0 | ditto | ditto |
| 2 | Polyethylene | 2.0 | ditto | ditto |
| 3 | Microcrystalline wax | 3.0 | ditto | ditto |
| 4 | Ceresin | 7.0 | ditto | ditto |
| 5 | Stearyl modified acryl silicone resin (Note 1) | 14.0 | ditto | ditto |
| 6 | Diphenyl dimethicone (Note 2) | 17.8 | ditto | ditto |
| 7 | Dissolved product (60% solution) of Example 1 | 6.0 | — | — |
| 8 | Dissolved product (60% solution) of Example 7 | | 6.0 | |
| 9 | Dissolved product (60% solution) of Comparative Example 1 | — | — | 6.0 |
| 10 | Alkyl-modified, branched polyglycerin-modified silicone (Note 3) | 3.0 | ditto | ditto |
| 11 | Macadamia nut oil | 10.0 | ditto | ditto |
| 12 | Hydrogenated polyisobutene | 8.0 | ditto | ditto |
| 13 | Isotridecyl isononanoate | 10.0 | ditto | ditto |
| 14 | Perfume | 0.2 | ditto | ditto |
| 15 | Lip stick pigment | 10 | ditto | ditto |
| 16 | Mica | 5 | ditto | ditto |
| Total | | 100 | ditto | ditto |

(Note 2)
KF-54; product of Shin-Etsu Chemical Co., Ltd.
(Note 1)
KP-561P; product of Shin-Etsu Chemical Co., Ltd.
(Note 3)
KF-6105; product of Shin-Etsu Chemical Co., Ltd.

<Preparation of a Cosmetic>

A: Components 1 to 12 were heated at 95 degrees C. and mixed uniformly.

B: Components 15 and 16 were dispersed in component 13 with a three-roll mill.

C: B was added to A at 85 degrees C. and uniformly mixed, to which Component 14 was then added and poured in a highly airtight container to obtain a lip stick.

The lip stick thus obtained was subjected to the following evaluation.

[Evaluation of Usability]

The lip sticks thus obtained were evaluated on spreadability, tackiness, uneven color in finish, and makeup retention (endurance at eight hours after application) by a panel of ten female experts, as in the aforesaid Examples.

TABLE 7

| Evaluation | Example 14 | Example 15 | Comparative Example 5 |
|---|---|---|---|
| Spreadability | A | B | C |
| Tackiness | A | A | B |
| Uneven color | A | A | C |
| Makeup retention | A | A | C |

Examples of cosmetics will hereinafter be shown. They were evaluated based on the criteria as those described above.

Example 16 Oily Mascara

<Preparation of a Cosmetic>

A: Components 1 to 9 were heated to 95 degrees C. and mixed uniformly.

B: Components 10 to 14 were uniformly mixed with a homodisper.

C: B was added to A and uniformly mixed at 90 degrees C., and the resulting mixture was slowly cooled to obtain an oily mascara.

| | Component | Mass % |
|---|---|---|
| 1. | Dissolved product (60% solution) of Example 9 | 12 |
| 2. | Trimethylsiloxysilicate dissolved in isododecane (Note 1) | 10 |
| 3. | Dextrin palmitate (Note 2) | 2 |
| 4. | Paraffin wax | 6 |
| 5. | Microcrystalline wax | 7 |
| 6. | Isododecane | 20 |
| 7. | Silicone-treated black iron oxide (Note 3) | 5 |
| 8. | Silicone-treated talc (Note 3) | 5 |
| 9. | Polymethylsilsesquioxane (Note 4) | 5 |
| 10. | Organo-modified clay mineral | 6 |
| 11. | Polyether-modified silicone having a branched silicone chain (Note 5) | 1.5 |
| 12. | Propylene carbonate | 1.6 |
| 13. | Methyl paraoxybenzoate | 0.1 |
| 14. | Isododecane | Balance |
| | Total | 100 |

(Note 1)
X-21-5595; product of Shin-Etsu Chemical Co., Ltd.
(Note 2)
Rheopearl KL2; product of Chiba Flour Milling Co., Ltd.
(Note 3)
Treated with KF-9909, product of Shin-Etsu Chemical Co., Ltd.
(Note 4)
KMP-590; product of Shin-Etsu Chemical Co., Ltd.
(Note 5)
KF-6028; product of Shin-Etsu Chemical Co., Ltd.

The oily mascara thus obtained was confirmed to provide a good feeling in use, long makeup retention, superior spreadability and finish appearance, and excellent rub-off resistance.

The use of trimethylsiloxysilicate which form a hard and brittle film makes it possible to control various film properties, feeling in use and finish appearance.

Example 17 W/O Mascara

<Preparation of a Cosmetic>

A: Components 1 to 7 were heated to 95 degrees C. and uniformly mixed.

B: Components 11 to 14 were uniformly mixed with a homodisper, and added to A, followed by heating to 90 degrees C.

C: Components 8 to 10 were added to B, heated to 85 degrees C., and mixed uniformly.

D: Components 15 to 17 were heated to 85 degrees C. and mixed uniformly.

E: D was added to C and emulsified, and the emulsion was gradually cooled to obtain a W/O oily mascara.

| | Component | Mass % |
|---|---|---|
| 1. | Dissolved product (60% solution) of Example 9 | 8 |
| 2. | Dissolved acrylate-silicone graft copolymer (Note 1) | 9 |
| 3. | Dextrin (palmitate/ethyl hexanoate) (Note 2) | 3 |
| 4. | Silicone wax (Note 3) | 5 |
| 5. | Ceresin | 2.5 |
| 6. | Beeswax | 4 |
| 7. | Diphenylsiloxy phenyl trimethicone (Note 4) | 3 |
| 8. | Silicone-treated black iron oxide (Note 5) | 5 |
| 9. | Silicone-treated talc (Note 5) | 4.5 |
| 10. | Amorphous silicic anhydride (Note 6) | 2.7 |
| 11. | Isododecane | Balance |
| 12. | Organo-modified clay mineral | 4 |
| 13. | Branched polyether-modified silicone (Note 7) | 2.2 |
| 14. | Propylene carbonate | 1.3 |
| 15. | Phenoxyethanol | 0.2 |
| 16. | 1,3-Butylene glycol | 2 |
| 17. | Purified water | 12.8 |
| | Total | 100 |

(Note 1)
KP-550; product of Shin-Etsu Chemical Co., Ltd.
(Note 2)
Rheopearl TT2; product of Chiba Flour Milling Co., Ltd.
(Note 3)
KP-562P; product of Shin-Etsu Chemical Co., Ltd.
(Note 4)
KF-56A; product of Shin-Etsu Chemical Co., Ltd.
(Note 5)
Treated with KF-9901; product of Shin-Etsu Chemical Co., Ltd.
(Note 6)
AEROSIL972; product of Nippon Aerosil Co., Ltd.
(Note 7)
KF-6017; product of Shin-Etsu Chemical Co., Ltd.

The W/O mascara thus obtained was confirmed to provide a good feeling in use, long makeup retention, superior spreadability and finish appearance, and excellent rub-off resistance. The use of silicone-modified acrylic polymer which forms film having flexibility makes it possible to control various film properties, feeling in use and finish appearance.

Example 18 Lip Stick

<Preparation of a Cosmetic>

A: Components 9 to 16 were treated with a three-roll mill to prepare a dispersion.

B: Components 1 to 8 were heated to 95 degrees C. and mixed uniformly.

C: A, B, and Components 17 to 18 were mixed uniformly and heated to 85 degrees C.

D: A stick container was filled with C to obtain a lip stick.

| | Component | Mass % |
|---|---|---|
| 1. | Synthetic wax | 7 |
| 2. | Paraffin wax | 3 |
| 3. | Silicone wax (Note 1) | 10.5 |
| 4. | Triethylhexanoin | 15.5 |
| 5. | Neopentyl glycol diethyl hexanoate | 14 |
| 6. | Neopentyl glycol dicaprate | 7 |
| 7. | Hydrogenated polyisobutene | 20 |
| 8. | Diphenyl dimethicone (Note 2) | 7.5 |
| 9. | Talc | 0.7 |
| 10. | Red 201 | q.s. |
| 11. | Red 202 | q.s. |
| 12. | Yellow 4 AL | q.s. |
| 13. | Silicone-treated titanium oxide (Note 3) | 3 |
| 14. | Silicone-treated black iron oxide (Note 3) | q.s. |
| 15. | Silicone-treated red iron oxide (Note 3) | q.s. |
| 16. | Diglyceryl triisostearate | 4 |
| 17. | Silicone-treated mica (Note 3) | 5.5 |
| 18. | Dissolved product (60% solution) of Example 2 | 1 |
| | Total | 100 |

(Note 1)
KP-561P; product of Shin-Etsu Chemical Co., Ltd.
(Note 2)
KF-54HV; product of Shin-Etsu Chemical Co., Ltd.
(Note 3)
Treated with KF-574; product of Shin-Etsu Chemical Co., Ltd.

The lip stick thus obtained was confirmed to provide a good feeling in use, long makeup retention, superior spreadability and finish appearance, and excellent rub-off resistance.

Example 19 W/O Sunscreen Milk

<Preparation of a Cosmetic>

A: Components 1 to 12 were mixed uniformly.

B: Components 15 to 21 were mixed uniformly.

C: B was added to A and emulsified, and Components 13 and 14 were added and the resulting mixture was mixed uniformly to obtain a W/O sunscreen milk.

| | Component | Mass % |
|---|---|---|
| 1. | Dissolved product (60% solution) of Example 3 | 3 |
| 2. | Phenyl-modified crosslinked dimethylpolysiloxane composition (Note 1) | 3 |
| 3. | Polyether-modified silicone having a branched alkyl and a branched silicone chain (Note 2) | 2 |
| 4. | Decamethylcyclopentasiloxane | 20 |
| 5. | Diphenylsiloxy phenyl trimethicone (Note 3) | 5.5 |
| 6. | Isononyl isononanoate | 5 |
| 7. | Stearyl glycyrrhetinate | 0.2 |
| 8. | BHT | 0.1 |
| 9. | 2-Ethylhexyl paramethoxycinnamate | 7.5 |
| 10. | Octocrylene | 2.5 |
| 11. | Hexyl 2-[4-(diethylamino)-2-hydroxybenzoyl] benzoate | 1 |
| 12. | Silicone composite powder (Note 4) | 0.5 |
| 13. | Superfine titanium oxide dispersion (Note 5) | 5 |
| 14. | Superfine zinc oxide dispersion (Note 6) | 10 |
| 15. | 1,3-Butylene glycol | 3 |
| 16. | Ethanol | 6 |
| 17. | Sodium citrate | 0.2 |
| 18. | Sodium hydroxide | q.s. |
| 19. | 2-Glucoside ascorbate | 2 |
| 20. | Ethylenediamine tetraacetate | 0.1 |
| 21. | Purified water | Balance |
| | Total | 100 |

(Note 1)
KSG-18A; product of Shin-Etsu Chemical Co., Ltd.
(Note 2)
KF-6038; product of Shin-Etsu Chemical Co., Ltd.
(Note 3)
KF-56A; product of Shin-Etsu Chemical Co., Ltd.
(Note 4)
KSP-105; product of Shin-Etsu Chemical Co., Ltd.
(Note 5)
PD-T7; product of Shin-Etsu Chemical Co., Ltd.
(Note 6)
SPD-25; product of Shin-Etsu Chemical Co., Ltd.

The W/O sunscreen milk thus obtained was confirmed to provide a good feeling in use, provide long makeup retention, and be excellent in spread.

Example 20 W/O Sunscreen Milk

<Preparation of a Cosmetic>

A: Components 1 to 7 were mixed uniformly.

B: Components 10 to 13 were mixed uniformly.

C: B was added to A and emulsified, and Components 8 and 9 were added and the resulting mixture was mixed uniformly to obtain a W/O sunscreen milk.

| | Component | Mass % |
|---|---|---|
| 1. | Dissolved product (60% solution) of Example 5 | 2 |
| 2. | Polyether-modified crosslinked silicone composition (Note 1) | 3 |
| 3. | Crosslinked dimethylpolysiloxane composition (Note 2) | 2 |
| 4. | Polyether-modified silicone having a branched silicone chain (Note 3) | 1 |
| 5. | Dimethylpolysiloxane (6 cs) | 5 |
| 6. | Decamethylcyclopentasiloxane | 3 |
| 7. | Isotridecyl isononanoate | 4 |
| 8. | Superfine titanium oxide dispersion (Note 4) | 25 |
| 9. | Superfine zinc oxide dispersion (Note 5) | 35 |
| 10. | Dipropylene glycol | 2 |
| 11. | Sodium citrate | 0.2 |
| 12. | Sodium chloride | 1 |
| 13. | Purified water | Balance |
| | Total | 100 |

(Note 1)
KSG-210; product of Shin-Etsu Chemical Co., Ltd.
(Note 2)
KSG-19; product of Shin-Etsu Chemical Co., Ltd.
(Note 3)
KF-6028; product of Shin-Etsu Chemical Co., Ltd.
(Note 4)
SPD-T5; product of Shin-Etsu Chemical Co., Ltd.
(Note 5)
SPD-25; product of Shin-Etsu Chemical Co., Ltd.

The W/O sunscreen milk thus obtained was confirmed to provide a good feeling in use, provide long makeup retention, and be excellent in spread.

Example 21 W/O Cream Foundation

<Preparation of a Cosmetic>

A: Components 9 to 12 were treated with a three-roll mill to prepare dispersion.

B: Components 3 to 5 were mixed uniformly and, then, Components 1, 2, and 6 to 8 were added and the resulting mixture was mixed uniformly.

C: Components 13 to 17 were mixed uniformly.

D: C was added to B and emulsified, and A was added to the emulsion to obtain a W/O cream foundation.

| | Component | Mass % |
|---|---|---|
| 1. | Alkyl-modified/polyether-modified crosslinked silicone composition (Note 1) | 3.5 |
| 2. | Alkyl-modified/crosslinked dimethylpolysiloxane composition (Note 2) | 6 |
| 3. | Polyether-modified silicone having a branched alkyl chain (Note 3) | 3 |
| 4. | Organo-modified clay mineral | 1.2 |
| 5. | Decamethylcyclopentasiloxane | 20 |
| 6. | 2-Ethylhexyl paramethoxycinnamate | 7.5 |
| 7. | Dissolved product (60% solution) of Example 6 | 2 |
| 8. | Phenyl-modified silicone composite powder (Note 4) | 2 |
| 9. | Ethylhexyl palmitate | 7 |
| 10. | Acrylate/silicone graft copolymer (Note 5) | 0.2 |
| 11. | Silicone-treated titanium oxide (Note 6) | 8.5 |
| 12. | Silicone-treated iron oxide (Note 7) | q.s. |
| 13. | 1,3-Butylene glycol | 5 |
| 14. | Methyl paraoxybenzoate | 0.15 |
| 15. | Sodium citrate | 0.2 |
| 16. | Sodium chloride | 0.5 |
| 17. | Purified water | Balance |
| | Total | 100 |

(Note 1)
KSG-330 product of Shin-Etsu Chemical Co., Ltd.
(Note 2)
KSG-41A; product of Shin-Etsu Chemical Co., Ltd.
(Note 3)
KF-6048; product of Shin-Etsu Chemical Co., Ltd.
(Note 4)
KSP-300; product of Shin-Etsu Chemical Co., Ltd.
(Note 5)
KP-578; product of Shin-Etsu Chemical Co., Ltd.
(Note 6)
KTP-09W; product of Shin-Etsu Chemical Co., Ltd.
(Note 7)
KTP-09Y, R, B; product of Shin-Etsu Chemical Co., Ltd.

The product thus obtained was confirmed to provide a good feeling in use, long makeup retention, superior spreadability and finish appearance, and excellent rub-off resistance.

Example 22 W/O Liquid Foundation

<Preparation of a Cosmetic>

A: Components 7 to 13 were treated with a homodisper to prepare dispersion.

B: Components 4 to 6 were mixed uniformly under heating, to which Components 1 to 3 were added and mixed uniformly.

C: Components 14 to 19 were mixed uniformly.

D: C was added to B and emulsified, and A was added to the emulsion to obtain a W/O liquid foundation.

| | Component | Mass % |
|---|---|---|
| 1. | Polyether-modified crosslinked silicone composition (Note 1) | 3.5 |
| 2. | Phenyl-modified/crosslinked dimethylpolysiloxane composition (Note 2) | 5 |
| 3. | Diphenylsiloxy phenyl trimethicone (Note 4) | 9 |
| 4. | Polyether-modified silicone having a branched silicone chain (Note 3) | 3 |
| 5. | Organo-modified clay mineral | 0.8 |
| 6. | Decamethylcyclopentasiloxane | 15 |
| 7. | Isopropyl myristate | 6 |
| 8. | Dissolved product (60% solution) of Example 4 | 1 |
| 9. | Metal soap-treated superfine titanium oxide (average primary particle size: 20 nm) | 5 |
| 10. | Alkylsilane-treated titanium oxide (Note 5) | 6.5 |
| 11. | Alkylsilane-treated yellow iron oxide (Note 5) | q.s. |
| 12. | Alkylsilane-treated red iron oxide (Note 5) | q.s. |
| 13. | Alkylsilane-treated black iron oxide (Note 5) | q.s. |
| 14. | Glycerin | 2 |
| 15. | Dipropylene glycol | 3 |
| 16. | Phenoxyethanol | 0.2 |
| 17. | Sodium citrate | 0.2 |
| 18. | Sodium chloride | 0.5 |
| 19. | Purified water | 37 |
| | Total | 100 |

(Note 1)
KSG-210; product of Shin-Etsu Chemical Co., Ltd.
(Note 2)
KSG-18A; product of Shin-Etsu Chemical Co., Ltd.
(Note 3)
KF-6028; product of Shin-Etsu Chemical Co., Ltd.
(Note 4)
KF-56A; product of Shin-Etsu Chemical Co., Ltd.
(Note 5)
Treated with AES-3083; product of Shin-Etsu Chemical Co., Ltd.

The W/O liquid foundation thus obtained was confirmed to provide a good feeling in use, long makeup retention, superior spreadability and finish appearance, and excellent rub-off resistance.

Example 23 W/O Stick Foundation

<Preparation of a Cosmetic>

A: Components 10 to 14 were treated with a three-roll mill to prepare dispersion.

B: Components 1 to 9 were heated to 95 degrees C. and mixed uniformly.

C: A and Components 15 and 16 were mixed uniformly and heated to 85 degrees C.

D: C was added to B and emulsified at 85 degrees C., and a stick container was filled with the resulting emulsion and was gradually cooled to obtain a W/O stick foundation.

| | Component | Mass % |
|---|---|---|
| 1. | Crosslinked polyglycerin-modified silicone composition (Note 1) | 4.5 |
| 2. | Polyether-modified silicone having a branched silicone chain and a branched alkyl chain (Note 2) | 1.5 |
| 3. | Inulin stearate (Note 3) | 1.8 |
| 4. | Ceresin | 6 |
| 5. | Neopentyl glycol diethyl hexanoate | 6 |
| 6. | Cetyl ethyl hexanoate | 4 |
| 7. | Dimethylpolysiloxane (6 cs) | 11.5 |
| 8. | Polymethylsilsesquioxane (Note 4) | 1.5 |
| 9. | Dissolved product (60% solution) of Example 2 | 1 |
| 10. | Silicone-treated titanium oxide (Note 5) | 6.5 |
| 11. | Silicone-treated iron oxide (Note 6) | q.s. |
| 12. | Polyether-modified silicone (Note 7) | 0.2 |

-continued

| | Component | Mass % |
|---|---|---|
| 13. | Polyether-modified silicone (Note 8) | 0.3 |
| 14. | Dipropylene glycol | 5 |
| 15. | Methyl paraoxybenzoate | 0.1 |
| 16. | Purified water | Balance |
| | Total | 100 |

(Note 1)
KSG-710; product of Shin-Etsu Chemical Co., Ltd.
(Note 2)
KF-6038; product of Shin-Etsu Chemical Co., Ltd.
(Note 3)
Rheopearl ISK2; product of Chiba Flour Milling Co., Ltd.
(Note 4)
KMP-590; product of Shin-Etsu Chemical Co., Ltd.
(Note 5)
KTP-09W; product of Shin-Etsu Chemical Co., Ltd.
(Note 6)
KTP-09R,Y,B; product of Shin-Etsu Chemical Co., Ltd.
(Note 7)
KF-6011; product of Shin-Etsu Chemical Co., Ltd.
(Note 8)
KF-6013; product of Shin-Etsu Chemical Co., Ltd.

The W/O stick foundation thus obtained was confirmed to provide a good feeling in use, long makeup retention, superior spreadability and finish appearance, and excellent rub-off resistance.

Example 24 Cast Foundation

<Preparation of a Cosmetic>

A: Components 10 to 14 were treated with a roll mill to prepare dispersion.

B: Components 1 to 7 were treated with a homodisper to prepare a dispersion, to which Components 8 and 9 were added and heated to 95 degrees C. and mixed uniformly.

C: A was added to B, mixed uniformly and heated to 85 degrees C.

D: C was poured into a container to obtain a cast foundation.

| | Component | Mass % |
|---|---|---|
| 1. | PG dicaprate | Balance |
| 2. | Dried-up product of Example 1 (Note 0) | 1 |
| 3. | Silicone composite powder (Note 1) | 10 |
| 4. | Silicone composite powder (Note 2) | 4 |
| 5. | Crosslinked dimethylpolysiloxane composition (Note 3) | 6 |
| 6. | Diphenylsiloxy phenyl trimethicone (Note 4) | 12 |
| 7. | Polyglycerin-modified silicone having a branched silicone chain and a branched alkyl chain (Note 5) | 0.5 |
| 8. | Paraffin wax | 6 |
| 9. | Polyethylene wax | 2 |
| 10. | Dimethicone (6 cs) | 11 |
| 11. | Silicone branched polyglycerin-modified silicone (Note 6) | 1 |
| 12. | Metal soap-treated superfine zinc oxide (average primary particle size: 30 nm) | 8 |
| 13. | Silicone-treated titanium oxide (Note 7) | 8.5 |
| 14. | Silicone-treated iron oxide (Note 8) | 1.5 |
| | Total | 100 |

(Note 0)
The product of Example 1 was dried up with a spray dryer to obtain a solid.
(Note 1)
KSP-101; product of Shin-Etsu Chemical Co., Ltd.
(Note 2)
KSP-105; product of Shin-Etsu Chemical Co., Ltd.
(Note 3)
KSG-16; product of Shin-Etsu Chemical Co., Ltd.
(Note 4)
KF-56A; product of Shin-Etsu Chemical Co., Ltd.
(Note 5)
KF-6105; product of Shin-Etsu Chemical Co., Ltd.
(Note 6)
KF-6106; product of Shin-Etsu Chemical Co., Ltd.
(Note 7)
KTP-09W; product of Shin-Etsu Chemical Co., Ltd.
(Note 8)
KTP-09R, Y, B; product of Shin-Etsu Chemical Co., Ltd.

The cast foundation thus obtained was confirmed to provide a good feeling in use, long makeup retention, superior spreadability and finish appearance, and excellent rub-off resistance.

Example 25 Eye Cream

<Preparation of a Cosmetic>

A: Components 1 to 4 were mixed uniformly.

B: Components 8 to 12 were mixed uniformly.

C: B was added to A and emulsified and, then, Components 5 to 7 were added and the resulting mixture was uniformly mixed to obtain an eye cream.

| | Component | Mass % |
|---|---|---|
| 1. | Silicone/alkyl-modified and polyether-modified crosslinked silicone composition (Note 1) | 4 |
| 2. | Silicone/alkyl-modified crosslinked dimethylpolysiloxane composition (Note 2) | 6 |
| 3. | Polyether-modified silicone having a branched silicone chain and a branched alkyl chain (Note 3) | 0.5 |
| 4. | Dimethicone (6 cs) | 12 |
| 5. | Vaseline | 4.5 |
| 6. | Dissolved product (60% solution) of Example 10 | 2.5 |
| 7. | Alkyl-modified silicone composite powder (Note 4) | 2 |
| 8. | 1,3-Butylene glycol | 7 |
| 9. | Phenoxyethanol | 0.25 |
| 10. | Sodium citrate | 0.2 |
| 11. | Sodium chloride | 0.5 |
| 12. | Purified water | Balance |
| | Total | 100 |

(Note 1)
KSG-350Z; product of Shin-Etsu Chemical Co., Ltd.
(Note 2)
KSG-045%; product of Shin-Etsu Chemical Co., Ltd.
(Note 3)
KF-6038; product of Shin-Etsu Chemical Co., Ltd.
(Note 4)
KSP-441; product of Shin-Etsu Chemical Co., Ltd.

The eye cream thus obtained was confirmed to provide a good feeling in use, allow a foundation layered on the eye cream to provide good makeup retention and finish appearance, and be excellent in spread.

Example 26 Wrinkle Concealer

<Preparation of a Cosmetic>

A: Components 1 to 7 were mixed uniformly.

B: Component 8 was added to A and the resulting mixture was mixed to obtain a wrinkle concealer.

| | Component | Mass % |
|---|---|---|
| 1. | Polyether-modified crosslinked silicone composition (Note 1) | 5 |
| 2. | Crosslinked dimethylpolysiloxane composition (Note 2) | 55 |
| 3. | Crosslinked dimethylpolysiloxane composition (Note 3) | 15 |
| 4. | Decamethylcyclopentasiloxane | Balance |
| 5. | Highly polymerized dimethylpolysiloxane/D5 mixed solution (Note 4) | 5 |
| 6. | Dissolved product (60% solution) of Example 8 | 1 |
| 7. | Silicone-modified polysaccharide compound solution (Note 6) | 1 |
| 8. | Silicone composite powder (Note 5) | 12 |
| | Total | 100 |

(Note 1)
KSG-210; product of Shin-Etsu Chemical Co., Ltd.
(Note 2)
KSG-15; product of Shin-Etsu Chemical Co., Ltd.
(Note 3)
KSG-016F; product of Shin-Etsu Chemical Co., Ltd.
(Note 4)
KF-9028; product of Shin-Etsu Chemical Co., Ltd.
(Note 5)
KSP-411; product of Shin-Etsu Chemical Co., Ltd.
(Note 6)
TSPL-30-D5; product of Shin-Etsu Chemical Co., Ltd.

The wrinkle concealer thus obtained was confirmed to provide a good feeling in use, provide long makeup retention, and be excellent in spread.

Example 27 W/O Sunscreen Cream

<Preparation of a Cosmetic>

A: Components 1 to 8 were mixed uniformly.

B: Components 9 to 15 were mixed uniformly.

C: B was added to A and the resulting mixture was emulsified to obtain a sunscreen.

| | Component | Mass % |
|---|---|---|
| 1. | Alkyl-modified and crosslinked polyglycerin-modified silicone composition (Note 1) | 3 |
| 2. | Alkyl-modified crosslinked dimethylpolysiloxane composition (Note 2) | 3 |
| 3. | Polyglycerin-modified silicone having a branched silicone chain and a branched alkyl chain (Note 3) | 1.5 |
| 4. | Diphenylsiloxy phenyl trimethicone (Note 4) | 11 |
| 5. | 2-Ethylhexyl paramethoxycinnamate | 6 |
| 6. | Octyl salicylate | 1 |
| 7. | Silicone composite powder (Note 5) | 2 |
| 8. | Dissolved product (60% solution) of Example 1 | 3 |
| 9. | Xanthan gum | 0.3 |
| 10. | Dipropylene glycol | 5 |
| 11. | Glycerin | 3 |
| 12. | Methyl paraoxybenzoate | 0.1 |
| 13. | 2K Glycyrrhizate | 0.2 |
| 14. | Sodium chloride | 0.5 |
| 15. | Purified water | Balance |
| | Total | 100 |

(Note 1)
KSG-840: product of Shin-Etsu Chemical Co., Ltd.
(Note 2)
KSG-43: product of Shin-Etsu Chemical Co., Ltd.
(Note 3)
KF-6105; product of Shin-Etsu Chemical Co., Ltd.
(Note 4)
KF-56A; product of Shin-Etsu Chemical Co., Ltd.
(Note 5)
KSP-100; product of Shin-Etsu Chemical Co., Ltd.

The W/O sunscreen cream thus obtained was found to provide a good feeling in use and excellent makeup retention.

Example 28 O/W Sunscreen Cream

<Preparation of a Cosmetic>

A: Components 1 to 6 were heated to 85 degrees C. and mixed uniformly.

B: Components 7 to 15 were heated to 85 degrees C. and mixed uniformly.

C: B was added to A and emulsified at 85 degrees C., and the resulting emulsion was gradually cooled while stirring to obtain a sunscreen.

| | Component | Mass % |
|---|---|---|
| 1. | Sodium hyaluronate | 0.1 |
| 2. | Ethanol | 10 |
| 3. | 1,3-Butylene glycol | 6 |
| 4. | Methyl paraoxybenzoate | 0.1 |
| 5. | Sodium acrylate/sodium acryloyldimethyl taurate copolymer composition (Note 1) | 2.5 |
| 6. | Purified water | Balance |
| 7. | Dissolved product (60% solution) of Example 2 | 1 |
| 8. | Diphenylsiloxy phenyl trimethicone (Note 2) | 3 |
| 9. | Crosslinked dimethylpolysiloxane composition (Note 3) | 1 |
| 10. | Cetanol | 2 |
| 11. | 2-Ethylhexyl paramethoxycinnamate | 5 |
| 12. | 2,4-Bis[{4-(2-ethylhexyloxy)-2-hydroxy}-phenyl]-6-(4-methoxyphenyl)-1,3,5-triazine | 1 |
| 13. | Polyoxyethylene (60) hydrogenated castor oil | 1 |
| 14. | Polyether-modified silicone (Note 4) | 0.5 |
| 15. | Tocopherol | 0.05 |
| | Total | 100 |

(Note 1)
SIMULGEL EG; product of SEPPIC
(Note 2)
KF-56A; product of Shin-Etsu Chemical Co., Ltd.
(Note 3)
KSG-016F; product of Shin-Etsu Chemical Co., Ltd.
(Note 4)
KF-6011; product of Shin-Etsu Chemical Co., Ltd.

The O/W sunscreen cream thus obtained was found to provide a good feeling in use and have excellent spreadability.

Example 29 Mousse Blush

<Preparation of a Cosmetic>

A: Components 1 to 6 were heated to 80 degrees C. and mixed uniformly.

B: Components 7 to 12 were mixed uniformly in a Henschel mixer.

C: B was added to A and uniformly mixed at 80 degrees C., and the resulting mixture was cooled gradually to obtain a mousse blush.

| | Component | Mass % |
|---|---|---|
| 1. | Crosslinked dimethylpolysiloxane composition (Note 1) | 32 |
| 2. | Decamethylcyclopentasiloxane | 30 |
| 3. | Neopentyl glycol diisostearate | 7 |
| 4. | Inulin stearate (Note 2) | 8 |
| 5. | Amorphous silicic anhydride (Note 3) | 0.5 |
| 6. | Dissolved product (60% solution) of Example 5 | 1.5 |
| 7. | Silicone-treated titanium oxide (Note 4) | 0.2 |
| 8. | Red 202 | q.s. |
| 9. | Silicone-treated yellow iron oxide (Note 4) | q.s. |
| 10. | Silicone-treated black iron oxide (Note 4) | q.s. |

-continued

| | Component | Mass % |
|---|---|---|
| 11. | Silicone-treated mica (Note 4) | 5.4 |
| 12. | Silicone-treated sericite (Note 4) | 10 |
| | Total | 100 |

(Note 1)
KSG-16; product of Shin-Etsu Chemical Co., Ltd.
(Note 2)
Rheopearl ISK2; product of Chiba Flour Milling Co., Ltd.
(Note 3)
AEROSIL200; product of Nippon Aerosil Co., Ltd.
(Note 4)
Treated with KP-574; product of Shin-Etsu ChemicalCo., Ltd.

The mousse blush thus obtained was found to provide a good feeling in use, long makeup retention, superior spreadability and finish appearance, and excellent rub-off resistance.

Example 30 Gel Eyeshadow

<Preparation of a Cosmetic>

A: Components 1 to 5 were heated to 80 degrees C. and mixed uniformly.

B: Components 6 to 9 were added to A, heated to 90 degrees C. and mixed uniformly.

C: The reaction mixture was poured in a container to obtain a gel eyeshadow.

| | Component | Mass % |
|---|---|---|
| 1. | Crosslinked dimethylpolysiloxane composition (Note 1) | 10.5 |
| 2. | Squalane | 17 |
| 3. | Dextrin palmitate (Note 2) | 8.5 |
| 4. | Isotridecyl isononanoate | Balance |
| 5. | Dissolved product (60% solution) of Example 6 | 3 |
| 6. | Amorphous silicic anhydride (Note 3) | 0.1 |
| 7. | Silicone composite powder (Note 4) | 5 |
| 8. | Barium sulfate | 9 |
| 9. | Silicone-treated mica titanium (Note 5) | 32.5 |
| | Total | 100 |

(Note 1)
KSG-16; product of Shin-Etsu Chemical Co., Ltd.
(Note 2)
Rheopearl KL2; product of Chiba Flour Milling Co., Ltd.
(Note 3)
AEROSIL972; product of Nippon Aerosil Co., Ltd.
(Note 4)
KSP-100; product of Shin-Etsu Chemical Co., Ltd.
(Note 5)
Treated with KP-574; product of Shin-Etsu Chemical Co., Ltd.

The gel eyeshadow thus obtained was found to provide a good feeling in use, long makeup retention, superior spreadability and finish appearance, and excellent rub-off resistance.

Example 31

Powder Foundation

<Preparation of a Cosmetic>

A: Components 1 to 4 were heated to 50 degrees C., mixed uniformly, and cooled to room temperature.

B: Components 5 to 14 were mixed uniformly.

C: A was added to B and mixed uniformly in a Henschel mixer. The powder thus obtained was filtered through a mesh and, then, the resulting powder was pressed in a mold to obtain a powder foundation.

| | Component | Mass % |
|---|---|---|
| 1. | 2-Ethylhexyl paramethoxycinnamate | 4 |
| 2. | Diphenylsiloxy phenyl trimethicone (Note 1) | 4.5 |
| 3. | Triethylhexanoin | 1.5 |
| 4. | Silicone wax (Note 2) | 1 |
| 5. | Dissolved product (60% solution) of Example 8 | 1 |
| 6. | Silicone-treated mica (Note 3) | 30 |
| 7. | Barium sulfate | 10 |
| 8. | Phenyl-modified silicone composite powder (Note 4) | 5 |
| 9. | Silicone composite powder (Note 5) | 4 |
| 10. | Silicone-treated talc (Note 3) | Balance |
| 11 | Silicone treated titanium oxide (Note 3) | 6 |
| 12. | Silicone-treated yellow iron oxide (Note 3) | q.s. |
| 13. | Silicone-treated red iron oxide (Note 3) | q.s. |
| 14. | Silicone-treated black iron oxide (Note 3) | q.s. |
| | Total | 100 |

(Note 1)
KF-56A; product of Shin-Etsu Chemical Co., Ltd.
(Note 2)
KP-561P; product of Shin-Etsu Chemical Co., Ltd.
(Note 3)
Treated with KF-9909; product of Shin-Etsu Chemical Co., Ltd.
(Note 4)
KSP-300; product of Shin-Etsu Chemical Co., Ltd.
(Note 5)
KSP-100; product of Shin-Etsu Chemical Co., Ltd.

The powder foundation thus obtained was found to provide a good feeling in use and long makeup retention, and be excellent in spreadability and finish appearance.

Example 32

Hair Treatment Agent to be Used Out of a Bath

<Preparation of a Cosmetic>

A: Components 1 to 4 were mixed uniformly.

B: Components 7 to 12 were mixed uniformly.

C: B was added to A and emulsified, and Components 5 and 6 were added to obtain a hair treatment agent to be used out of a bath.

| | Component | Mass % |
|---|---|---|
| 1. | Crosslinked polyglycerin-modified silicone composition (Note 1) | 3 |
| 2. | Crosslinked dimethylpolysiloxane composition (Note 2) | 1 |
| 3. | Polyether-modified silicone (Note 3) | 0.2 |
| 4. | Dimethylpolysiloxane (6 cs) | 8 |
| 5. | Perfume | q.s. |
| 6. | Dissolved product (60% solution) of Example 10 | 1 |
| 7. | Dipropylene glycol | 8 |
| 8. | Ethanol | 5 |
| 9. | Methyl paraoxybenzoate | 0.1 |
| 10. | Sodium citrate | 0.2 |
| 11 | Sodium chloride | 0.5 |
| 12. | Purified water | Balance |
| | Total | 100 |

(Note 1)
KSG-210; product of Shin-Etsu Chemical Co., Ltd.
(Note 2)
KSG-19; product of Shin-Etsu Chemical Co., Ltd.
(Note 3)
KF-6017; product of Shin-Etsu Chemical Co., Ltd.

The hair treatment agent thus obtained was found to spread lightly, give luster to the hair and be excellent in smoothness.

Example 33

Hair Treatment Agent

<Preparation of a Cosmetic>

A: Components 6 to 9 were heated to 70 degrees C. and mixed uniformly.

B: Components 1 to 5 were heated to 70 degrees C. and mixed uniformly.

C: B was added to A, emulsified and gradually cooled and, then, Components 10 and 11 were added to obtain a treatment agent.

| | Component | Mass % |
|---|---|---|
| 1. | Dissolved product (60% solution) of Example 9 | 0.5 |
| 2. | Cetanol | 2 |
| 3. | Cetyl octanoate | 3 |
| 4. | Butyl paraoxybenzoate | 0.1 |
| 5. | Diphenylsiloxy phenyl trimethicone (Note 1) | 1 |
| 6. | Behentrimonium chloride | 1 |
| 7. | Propylene glycol | 5 |
| 8. | Hydroxyethyl cellulose | 0.1 |
| 9. | Purified water | Balance |
| 10. | Amino-modified silicone emulsion (Note 2) | 4 |
| 11. | Perfume | q.s. |
| | Total | 100 |

(Note 1)
KF-56A; product of Shin-Etsu Chemical Co., Ltd.
(Note 2)
X-52-2328; product of Shin-Etsu Chemical Co., Ltd.

The hair treatment agent thus obtained was found to spread lightly, give luster to the hair and have excellent in smoothness.

Example 34 Hair Oil

<Preparation of a Cosmetic>

A: Components 1 to 7 were mixed uniformly to obtain a hair oil.

| | Component | Mass % |
|---|---|---|
| 1. | Dissolved product (60% solution) of Example 10 | 3 |
| 2. | Diphenylsiloxy phenyl trimethicone (Note 1) | 7 |
| 3. | Diethyl hexyl succinate | 10 |
| 4. | Highly polymerized dimethiconol mixed solution (Note 2) | 1.5 |
| 5. | Tocopherol | 0.1 |
| 6. | Perfume | 0.1 |
| 7. | Light liquid isoparaffin | Balance |
| | Total | 100 |

(Note 1)
KF-56A; product of Shin-Etsu Chemical Co., Ltd.
(Note 2)
X-21-5613; product of Shin-Etsu Chemical Co., Ltd.

The hair oil thus obtained was found to spread lightly, give luster to the hair, and be excellent in smoothness.

Example 35 Hair Wax

<Preparation of a Cosmetic>

A: Components 1 to 9 were heated to 80 degrees C. and mixed uniformly.

B: Components 10 to 16 were heated to 90 degrees C. and mixed uniformly.

C: B was added to A and emulsified at 80 degrees C. and, then, the emulsion was cooled to room temperature.

D: Components 17 to 19 were added to C and mixed uniformly to obtain a hair wax.

| | Component | Mass % |
|---|---|---|
| 1. | Dissolved product (60% solution) of Example 10 | 1 |
| 2. | Methyl trimethicone (Note 1) | 10 |
| 3. | *Candelilla* wax | 14 |
| 4. | Beeswax | 6 |
| 5. | POE glyceryl isostearate | 2 |
| 6. | Glycerin monostearate | 3 |
| 7. | Polyether-modified silicone (Note 2) | 2 |
| 8. | Stearic acid | 2 |
| 9. | 2-Ethylhexyl paramethoxycinnamate | 0.1 |
| 10. | Propylene glycol | 6 |
| 11. | 1,3-Butylene glycol | 6 |
| 12. | Methyl paraoxybenzoate | 0.2 |
| 13. | Phenoxyethanol | 0.3 |
| 14. | Sodium edetate | q.s. |
| 15. | Purified water | 31 |
| 16. | Potassium hydroxide (10% solution) | q.s. |
| 17. | Carboxyvinyl polymer (2% solution) | 15 |
| 18. | Potassium hydroxide (10% solution) | q.s. |
| 19. | Perfume | q. s. |
| | Total | 100 |

(Note 1)
TMF-1.5; product of Shin-Etsu Chemical Co., Ltd.
(Note 2)
KF-6011; product of Shin-Etsu Chemical Co., Ltd.

The hair wax thus obtained was found to be less tacky and have excellent hair holding ability and anti-sweat resistance.

Example 36

Shampoo

<Preparation of a Cosmetic>

A: Components 1 to 10 were uniformly mixed at 70 degrees C. and gradually cooled to obtain a shampoo.

| | Component | Mass % |
|---|---|---|
| 1. | Dissolved product (60% solution) of Example 10 | 0.5 |
| 2. | Polyoxyethylene lauryl ether | 0.5 |
| 3. | Glycol distearate | 2 |
| 4. | Sodium methyl cocoyl taurate | 8 |
| 5 | Cocamidopropyl betaine | 8 |
| 6. | Sodium lauryl sulfate | 10 |
| 7. | Cationized cellulose | 0.5 |
| 8. | Perfume | 0.1 |
| 9. | Methylparaben | 0.1 |
| 10. | Purified water | Balance |
| | Total | 100 |

The shampoo thus obtained was found to permit smooth combing with fingers, give luster to the hair, and smoothness to the hair.

Example 37

Roll-on Antiperspirant

<Preparation of a Cosmetic>

A: Components 1 to 4 were mixed uniformly.

B: Components 5 to 11 were mixed uniformly.

C: B was added to A and emulsified to obtain a roll-on antiperspirant.

| | Component | Mass % |
|---|---|---|
| 1. | Polyether-modified crosslinked silicone composition (Note 1) | 5 |
| 2. | Polyether-modified silicone having a branched silicone chain (Note 2) | 0.8 |
| 3. | Dissolved product (60% solution) of Example 5 | 5 |
| 4. | Decamethylcyclopentasiloxane | 9 |
| 5. | 1,3-Butylene glycol | 5 |
| 6. | Aluminum chlorohydrate | 10 |
| 7. | Benzalkonium chloride | 0.2 |
| 8. | Menthol | 0.05 |
| 9. | Ethanol | 15 |
| 10. | Perfume | q. s. |
| 11. | Purified water | Balance |
| | Total | 100 |

(Note 1)
KSG-210; product of Shin-Etsu Chemical Co., Ltd.
(Note 2)
KF-6028; product of Shin-Etsu Chemical Co., Ltd.

The roll-on antiperspirant thus obtained was found to spread lightly, not to whiten the skin, and to have a lasting antiperspirant effect.

Example 38

Nail Enamel Overcoat

<Preparation of a Cosmetic>

A: Components 5 to 9 were mixed and, then, Component 4 was added and was mixed uniformly.

B: Components 1 to 3 were added to A and mixed to obtain a nail enamel overcoat.

| | Component | Mass % |
|---|---|---|
| 1. | Dissolved product (60% solution) of Example 9 | 5 |
| 2. | Nitrocellulose | 17 |
| 3. | Alkyd resin | 4 |
| 4. | Acetyl triethyl citrate | 5 |
| 5. | Butyl acetate | 29 |
| 6. | Ethyl acetate | 25 |
| 7. | Isopropyl alcohol | 3 |
| 8. | n-Butyl alcohol | 1 |
| 9. | Toluene | Balance |
| | Total | 100 |

The enamel overcoat thus obtained was found to spread lightly, enhance the luster of the enamel and be excellent in endurance.

The invention claimed is:

1. A crosslinked organosilicone resin represented by the following average composition formula (1):

$$(R^1_3SiO_{1/2})_{a1}(R^2_3SiO_{1/2})_{a2}(R^3_3Si_{1/2})_{a3}(R^1_{3-p}(X_{1/2})_pSiO_{1/2})_{a4}(R^1_2SiO_{2/2})_b(R^1SiO_{3/2})_c(SiO_{4/2})_d \quad (1)$$

wherein $R^1$ is, independently of each other, a substituted or unsubstituted, monovalent hydrocarbon group having 1 to 30 carbon atoms and having no aliphatic unsaturated bond, $R^2$ is, independently of each other, a polyoxyalkylene-containing group, a polyglycerin-containing group, or a group selected from the groups defined for $R^1$ and at least one of $R^2$ in each of the $R^2_3SiO_{1/2}$ units is a polyoxyalkylene-containing group or a polyglycerin-containing group, $R^3$ is, independently of each other, an organopolysiloxane-containing group or a group selected from the groups defined for $R^1$ and at least one of $R^3$ in each of the $R^3SiO_{1/2}$ units is an organopolysiloxane-containing group, X is a divalent group represented by the following formula (2) or (3):

(2)

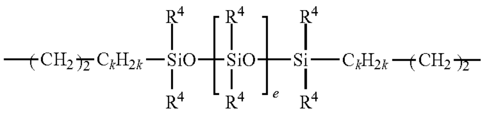

wherein $R^4$ is, independently of each other, a substituted or unsubstituted, monovalent hydrocarbon group having 1 to 30 carbon atoms and having no aliphatic unsaturated bond, e is an integer of $0 \leq e \leq 500$ and k is an integer of $0 \leq k \leq 5$;

$$—(CH_2)_2—C_fH_{2f}—(CH_2)_2— \quad (3)$$

wherein f is an integer of $0 \leq f \leq 20$;

optionally, a part of $R^2$, $R^3$ and X may be a hydroxyl group, a1, a2, a3, a4, b, c, and d satisfy the equations, $0<a1 \leq 400$, $0 \leq a2 \leq 200$, $0 \leq a3 \leq 400$, $0<a4 \leq 50$, $0 \leq b \leq 320$, $0 \leq c \leq 320$, $0<d \leq 1{,}000$ and $0.5 \leq (a1+a2+a3+a4)/d \leq 1.5$ and p is an integer of $1 \leq p \leq 3$.

2. The crosslinked organosilicone resin according to claim 1, wherein the polyoxyalkylene-containing group for $R^2$ is represented by the following formula (4):

$$—(CH_2)_2—C_mH_{2m}—O—(C_2H_4O)_{g1}(C_3H_6O)_{g2}R^5 \quad (4)$$

wherein $R^5$ is an unsubstituted or substituted, monovalent hydrocarbon group having 1 to 30 carbon atoms or a hydrogen atom and m, g1 and g2 are integers satisfying the equations, $0 \leq m \leq 15$, $0 \leq g1<200$, $0 \leq g2<200$ and $0<g1+g2 \leq 200$.

3. The crosslinked organosilicone resin according to claim 1, wherein the polyglycerin-containing group for $R^2$ is represented by the following formula (5):

$$—(CH_2)_2—C_mH_{2m}—O—(CH_2CH(OH)CH_2O)_hR^5 \quad (5)$$

wherein $R^5$ is an unsubstituted or substituted, monovalent hydrocarbon group having 1 to 30 carbon atoms or a hydrogen atom; and m and h are integers satisfying the equations, $0 \leq m \leq 15$ and $0<h \leq 5$.

4. The crosslinked organosilicone resin according to claim 1, wherein the organopolysiloxane-containing group for $R^3$ is a group represented by the following formula (6), (7), (8), or (9):

$$—(CH_2)_2—C_nH_{2n}—(SiOR^6_2)_i—SiR^6_3 \quad (6)$$

$$—(CH_2)_2—C_nH_{2n}—SiR^6_{j1}—(OSiR^6_3)_{3-j1} \quad (7$$

$$—(CH_2)_2—C_nH_{2n}—SiR^6_{j1}—(OSiR^6_{j2}(OSiR^6_3)_{3-j2})_{3-j1} \quad (8)$$

$$—(CH_2)_2—C_nH_{2n}—SiR^6_{j1}—(OSiR^6_{j2}(OSiR^6_{j3}(OSiR^6_3)_{3-j3})_{3-j2})_{3-j1} \quad (9)$$

wherein $R^6$ is, independently of each other, a substituted or unsubstituted, monovalent hydrocarbon group having 1 to 30 carbon atoms and having no aliphatic unsaturated bond; n and i are integers satisfying equations, $0 \leq n \leq 5$ and $0 \leq i \leq 500$; and $j_1$ to $j_3$ are integers of 0 to 2.

5. The crosslinked organosilicone resin according to claim 1, the resin having a weight average molecular weight of from 1,000 to 1,000,000.

6. The crosslinked organosilicone resin according to claim 1, wherein at least one of X in the average composition formula (1) is a group represented by said formula (2), a4 in the average composition formula (1) satisfies the equation, $0<a4\leq 5$, e in the formula (2) satisfies the equation, $0<e<40$, and the crosslinked organosilicone resin is solid at 25 degrees C.

7. The crosslinked organosilicone resin according to claim 1, wherein at least one of X in the average composition formula (1) is a group represented by the formula (2), a4 in the average composition formula (1) satisfies the equation, $0<a4\leq 3$, e in the formula (2) satisfies the equation, $0<e\leq 20$, and the crosslinked organosilicone resin is solid at 25 degrees C.

8. The crosslinked organosilicone resin according to claim 2, wherein the polyglycerin-containing group for $R^2$ is represented by the following formula (5):

$$-(CH_2)_2-C_mH_{2m}-O-(CH_2CH(OH)CH_2O)_hR^5 \quad (5)$$

wherein $R^5$ is an unsubstituted or substituted, monovalent hydrocarbon group having 1 to 30 carbon atoms or a hydrogen atom; and m and h are integers satisfying the equations, $0\leq m\leq 15$ and $0<h\leq 5$.

9. The crosslinked organosilicone resin according to claim 2, wherein the organopolysiloxane-containing group for $R^3$ is a group represented by the following formula (6), (7), (8), or (9):

$$-(CH_2)_2-C_nH_{2n}-(SiOR^6{}_2)_i-SiR^6{}_3 \quad (6)$$

$$-(CH_2)_2-C_nH_{2n}-SiR^6{}_{j1}-(OSiR^6{}_3)_{3-j1} \quad (7$$

$$-(CH_2)_2-C_nH_{2n}-SiR^6{}_{j1}-(OSiR^6{}_{j2}(OSiR^6{}_3)_{3-j2})_{3-j1} \quad (8)$$

$$-(CH_2)_2-C_nH_{2n}-SiR^6{}_{j1}-(OSiR^6{}_{j2}(OSiR^6{}_{j3}(OSiR^6{}_3)_{3-j3})_{3-j2})_{3-j1} \quad (9)$$

wherein $R^6$ is, independently of each other, a substituted or unsubstituted, monovalent hydrocarbon group having 1 to 30 carbon atoms and having no aliphatic unsaturated bond; n and i are integers satisfying equations, $0\leq n\leq 5$ and $0\leq i\leq 500$; and $j_1$ to $j_3$ are integers of 0 to 2.

10. The crosslinked organosilicone resin according to claim 2, the resin having a weight average molecular weight of from 1,000 to 1,000,000.

11. The crosslinked organosilicone resin according to claim 2, wherein at least one of X in the average composition formula (1) is a group represented by said formula (2), a4 in the average composition formula (1) satisfies the equation, $0<a4\leq 5$, e in the formula (2) satisfies the equation, $0<e<40$, and the crosslinked organosilicone resin is solid at 25 degrees C.

* * * * *